(12) United States Patent
Vaisnys et al.

(10) Patent No.: US 8,116,863 B2
(45) Date of Patent: Feb. 14, 2012

(54) SYSTEM AND METHOD FOR EFFECTIVELY INDICATING ELEMENT FAILURE OR A PREVENTIVE MAINTENANCE CONDITION IN AN AUTOMATIC EXTERNAL DEFIBRILLATOR (AED)

(75) Inventors: Gintaras A. Vaisnys, Guilford, CT (US); Giovanni C. Meier, Guilford, CT (US); Glenn W. Laub, Guilford, CT (US); Michael S. Hicks, Guilford, CT (US)

(73) Assignee: Defibtech, LLC, Guilford, CT (US)

( * ) Notice: Subject to any disclaimer, the term of this patent is extended or adjusted under 35 U.S.C. 154(b) by 733 days.

(21) Appl. No.: 11/949,469

(22) Filed: Dec. 3, 2007

(65) Prior Publication Data

US 2008/0136652 A1   Jun. 12, 2008

Related U.S. Application Data

(63) Continuation-in-part of application No. 11/386,057, filed on Mar. 21, 2006, now Pat. No. 7,548,781.

(51) Int. Cl.
*A61N 1/39* (2006.01)
(52) U.S. Cl. .......................................................... 607/5
(58) Field of Classification Search ........................ 607/5
See application file for complete search history.

(56) References Cited

U.S. PATENT DOCUMENTS

| | | |
|---|---|---|
| 4,101,787 A | 7/1978 | Vail |
| 4,590,943 A | 5/1986 | Paull et al. |
| 5,224,870 A | 7/1993 | Weaver et al. |
| 5,314,451 A | 5/1994 | Mulier |
| 5,350,317 A | 9/1994 | Weaver et al. |
| 5,372,605 A | 12/1994 | Adams et al. |
| 5,470,343 A | 11/1995 | Fincke et al. |
| 5,483,165 A | 1/1996 | Cameron et al. |
| 5,562,710 A | 10/1996 | Olsen et al. |
| 5,579,234 A * | 11/1996 | Wiley et al. ................. 702/118 |
| 5,591,213 A | 1/1997 | Morgan et al. |
| 5,593,426 A | 1/1997 | Morgan et al. |
| 5,640,078 A | 6/1997 | Kou et al. |
| 5,645,571 A | 7/1997 | Olson et al. |
| 5,658,316 A | 8/1997 | Lamond et al. |
| 5,697,955 A | 12/1997 | Stolte |
| 5,700,281 A | 12/1997 | Brewer et al. |
| 5,721,482 A | 2/1998 | Benvegar et al. |
| 5,741,305 A | 4/1998 | Vincent et al. |
| 5,749,902 A | 5/1998 | Olson et al. |
| 5,773,961 A | 6/1998 | Cameron et al. |

(Continued)

OTHER PUBLICATIONS

Hewlett Packard, 43110 A Defibrillator/Monitor Operating Guide, Eighth Edition, pp. 2, 5, 36-39, Aug. 1991.

(Continued)

*Primary Examiner* — Carl H Layno
*Assistant Examiner* — Paula J Stice
(74) *Attorney, Agent, or Firm* — King & Spalding LLP

(57) ABSTRACT

Battery powered systems with long standby times, such as automatic external defibrillators (AEDs), may be required to indicate their operational status to a user by blinking lights or sounding speakers or buzzers. These active status indication activities consume power thereby reducing the battery life of the system. To conserve power and to be more effective in seeking attention from a human operator, the status alerts for the AED produced by an active status indicator (ASI) system can be more meaningful to humans or more unique relative to status alerts provided by conventional devices. Additionally, the ASI system may automatically adjust power consumed by the indicators in response to sensing environmental conditions of the AED.

30 Claims, 14 Drawing Sheets

U.S. PATENT DOCUMENTS

| | | | |
|---|---|---|---|
| 5,782,878 | A | 7/1998 | Morgan et al. |
| 5,791,907 | A | 8/1998 | Ramshaw et al. |
| 5,792,190 | A | 8/1998 | Olson et al. |
| 5,797,969 | A | 8/1998 | Olson et al. |
| 5,800,460 | A | 9/1998 | Powers et al. |
| 5,817,151 | A | 10/1998 | Olson et al. |
| D405,754 | S | 2/1999 | Barkley et al. |
| 5,868,790 | A | 2/1999 | Vincent et al. |
| 5,868,794 | A | 2/1999 | Barkley et al. |
| 5,879,374 | A | 3/1999 | Powers et al. |
| 5,889,388 | A | 3/1999 | Cameron et al. |
| 5,897,576 | A | 4/1999 | Olson et al. |
| D409,752 | S | 5/1999 | Bishay et al. |
| 5,904,707 | A | 5/1999 | Ochs et al. |
| 5,913,685 | A | 6/1999 | Hutchins |
| 5,919,212 | A | 7/1999 | Olson et al. |
| 5,929,601 | A | 7/1999 | Kaib et al. |
| 5,944,741 | A | 8/1999 | Ochs et al. |
| 5,955,956 | A | 9/1999 | Stendahl et al. |
| 5,964,786 | A | 10/1999 | Ochs et al. |
| 5,983,137 | A | 11/1999 | Yerkovich |
| 5,999,493 | A | 12/1999 | Olson |
| 6,016,059 | A | 1/2000 | Morgan |
| 6,021,352 | A | 2/2000 | Christopherson et al. |
| 6,038,473 | A | 3/2000 | Olson et al. |
| 6,075,345 | A | 6/2000 | Lee |
| 6,101,413 | A | 8/2000 | Olson et al. |
| 6,141,584 | A | 10/2000 | Rockwell et al. |
| 6,148,233 | A | 11/2000 | Owen et al. |
| 6,152,754 | A | 11/2000 | Gerhardt et al. |
| 6,169,387 | B1 | 1/2001 | Kaib |
| 6,201,992 | B1 | 3/2001 | Freeman |
| 6,219,569 | B1 | 4/2001 | Kelly et al. |
| 6,230,053 | B1 | 5/2001 | Magin |
| 6,263,245 | B1 | 7/2001 | Snell |
| 6,278,366 | B1 | 8/2001 | Fletcher et al. |
| 6,301,502 | B1 | 10/2001 | Owen et al. |
| 6,304,780 | B1 | 10/2001 | Owen et al. |
| 6,314,320 | B1 | 11/2001 | Powers et al. |
| 6,334,070 | B1 | 12/2001 | Nova et al. |
| 6,363,282 | B1 | 3/2002 | Nichols et al. |
| 6,366,809 | B1 | 4/2002 | Olson et al. |
| 6,370,428 | B1 | 4/2002 | Snyder et al. |
| 6,374,137 | B1 | 4/2002 | Morgan et al. |
| 6,374,138 | B1 | 4/2002 | Owen et al. |
| 6,381,492 | B1 | 4/2002 | Rockwell et al. |
| 6,386,882 | B1 | 5/2002 | Linberg |
| 6,397,104 | B1 | 5/2002 | Miller et al. |
| 6,405,083 | B1 | 6/2002 | Rockwell et al. |
| 6,418,342 | B1 | 7/2002 | Owen et al. |
| 6,427,083 | B1 | 7/2002 | Owen et al. |
| 6,438,417 | B1 | 8/2002 | Rockwell et al. |
| 6,442,433 | B1 | 8/2002 | Linberg |
| 6,480,745 | B2 | 11/2002 | Nelson |
| 6,497,655 | B1 | 12/2002 | Linberg et al. |
| 6,546,285 | B1 | 4/2003 | Owen et al. |
| 6,586,850 | B1 | 7/2003 | Powers |
| 6,597,948 | B1 | 7/2003 | Rockwell et al. |
| 6,623,312 | B2 | 9/2003 | Merry et al. |
| 6,648,823 | B2 | 11/2003 | Thompson |
| 6,650,942 | B2 | 11/2003 | Howard et al. |
| 6,671,545 | B2 | 12/2003 | Fincke |
| 6,681,899 | B1 | 1/2004 | Hong |
| 6,697,671 | B1 | 2/2004 | Nova et al. |
| 6,754,538 | B2 | 6/2004 | Linberg |
| 6,799,072 | B2 | 9/2004 | Ries et al. |
| 6,820,998 | B2 | 11/2004 | Chen |
| 6,871,093 | B2 | 3/2005 | Hansen |
| 6,878,112 | B2 | 4/2005 | Linberg et al. |
| 6,920,360 | B2 | 7/2005 | Lee et al. |
| 6,944,498 | B2 | 9/2005 | Owen et al. |
| 6,955,864 | B1 | 10/2005 | Vaisnys et al. |
| 6,978,182 | B2 | 12/2005 | Mazar et al. |
| 6,990,371 | B2 | 1/2006 | Powers et al. |
| 6,993,386 | B2 | 1/2006 | Lin et al. |
| 2002/0032470 | A1 | 3/2002 | Linberg et al. |
| 2002/0082644 | A1 | 6/2002 | Picardo et al. |
| 2002/0087195 | A1 * | 7/2002 | Hansen ............................ 607/5 |
| 2002/0095196 | A1 | 7/2002 | Linberg et al. |
| 2003/0004547 | A1 | 1/2003 | Owen et al. |
| 2003/0055460 | A1 | 3/2003 | Owen et al. |
| 2003/0068914 | A1 | 4/2003 | Merry et al. |
| 2003/0144711 | A1 | 7/2003 | Pless et al. |
| 2003/0205988 | A1 | 11/2003 | Vaisnys et al. |
| 2004/0059405 | A1 | 3/2004 | White et al. |
| 2004/0122488 | A1 | 6/2004 | Mazar et al. |
| 2004/0133244 | A1 | 7/2004 | Vaisnys et al. |
| 2004/0143298 | A1 | 7/2004 | Nova et al. |
| 2004/0215278 | A1 | 10/2004 | Stegink et al. |
| 2005/0036294 | A1 | 2/2005 | McMahon |
| 2005/0137653 | A1 | 6/2005 | Friedman et al. |
| 2005/0159787 | A1 | 7/2005 | Linberg et al. |
| 2005/0225983 | A1 | 10/2005 | Fornell |
| 2005/0261742 | A1 | 11/2005 | Nova et al. |

OTHER PUBLICATIONS

Agilent Heartstream FR2, M3860A, M3861A, User's Guide, pp. 2-1-2-2, 2-4, 4-5, and B6, 2000.

Medtronic Physio-Control, Lifepack.RTM. 500 automated external defibrillator, Service Manual, pp. 3 of 124-12, 7 of 12-10 of 12, 12 of 12, 2001.

Medtronic Physio-Control, Lifepak.RTM. 500 Automated External Defibrillator Operating Instructions, pp. 25-2-6, 5-7-5-11, 5-16-5-17, Mar. 2001.

Survivalink FirstSave.TM. Operation and Service Manual, pp. 20, 29-31, 65, 70,84 and 85, 2000.

Swerdlow et al., "Cardiovascular Collapse Caused by Electrocardiographically Silent 60-Hz Intracardiac Leakage Current", 1999, American Heart Association, pp. 1-13.

* cited by examiner

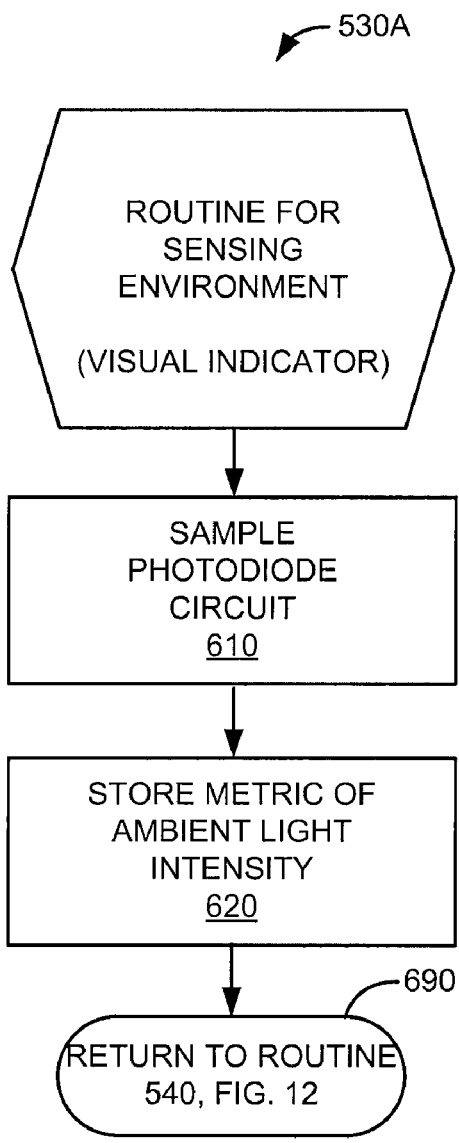
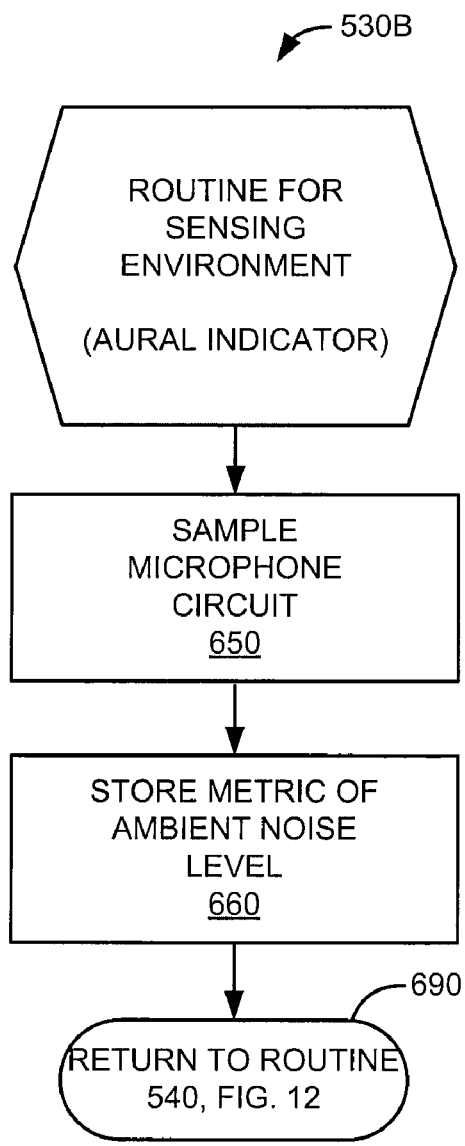
FIG. 13A
FIG. 13B

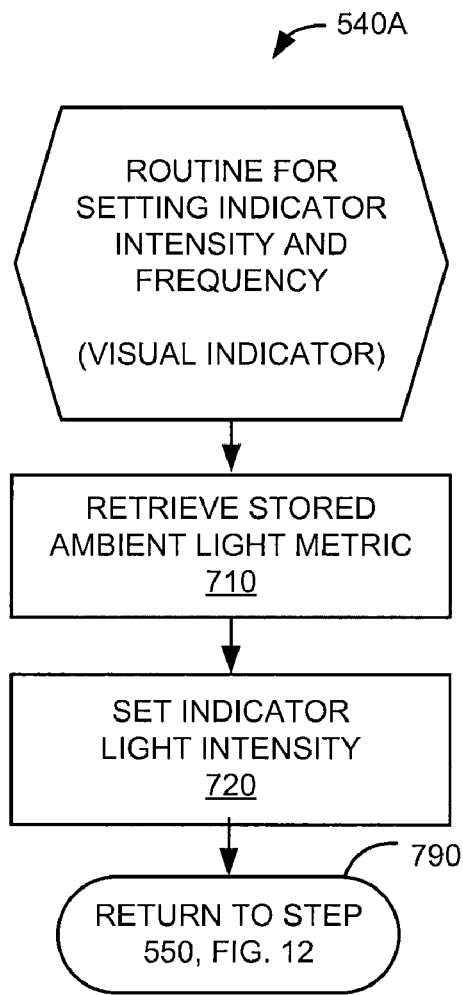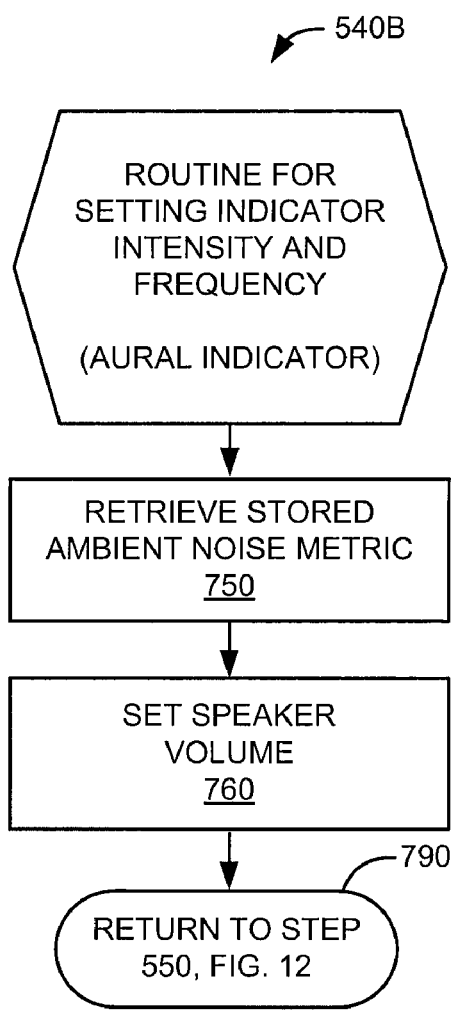
FIG. 14A
FIG. 14B

SYSTEM AND METHOD FOR EFFECTIVELY INDICATING ELEMENT FAILURE OR A PREVENTIVE MAINTENANCE CONDITION IN AN AUTOMATIC EXTERNAL DEFIBRILLATOR (AED)

CROSS REFERENCE TO RELATED APPLICATION FOR WHICH A BENEFIT IS CLAIMED UNDER 35 U.S.C. §120

This patent application is a continuation-in-part of and claims priority under 35 U.S.C. §120 to U.S. Non-Provisional patent application Ser. No. 11/386,057, now U.S. Pat. No. 7,548,781, entitled "Environmentally Responsive Active Status Indicator System and Method," filed on Mar. 21, 2006. The complete disclosure of the above identified priority application is hereby fully incorporated herein by reference.

TECHNICAL FIELD

The present invention is generally directed to battery-powered cardiac defibrillation systems, and relates more particularly to status indicators of portable AEDs that conserve battery power while providing meaningful alerts that attract human attention.

BACKGROUND OF THE INVENTION

Automatic external defibrillators (AEDs) are defibrillators that are designed to be operated by users with minimal training. Because AEDs can be used by non-medical personnel to treat sudden cardiac arrest (SCA), they are being deployed in a myriad of locations outside of traditional medical settings. As a result, more and more non-medical establishments are purchasing AEDs for deployment in their environments. AEDs are typically powered by stand alone battery systems.

AEDs are typically standby devices that are used infrequently and that remain in storage for long periods of time. This standby storage time can be on the order of months or even years. Minimizing power consumed by the AED while it is in standby mode during storage may extend the battery life of the system and reserve battery power for rescue attempts using the AED.

Since AEDs are in standby mode for long periods of time, knowing the operational status of a standby AED is very important. The operational status of an AED can be determined by various internal self tests. These tests may cover general operations of hardware and software, battery life, etc. The results of these tests can be communicated to a user via visual or aural indicators even while the AED is in a low power standby mode.

In such a system, there can be a status circuit or apparatus inside the AED that can report the status of the AED system. More generally, the AED may be referred to as the host system or host device. Various systems other than AEDs have similar low power consumption requirements for status indicators. Such systems may be referred to as host systems or host devices when they include status circuits that indicate the status of the host system.

Status indicators for host systems may be passive or active. An active indicator is one that may require power to be expended for it to continue to indicate, such as an indicator light. A passive indicator may continue to indicate without consuming additional power. For example, an indicator that mechanically changes colors by physically flipping an internal element that can be seen by a user through a window may be a passive indicator. Once the internal element of the passive indicator is physically flipped, it will stay in that state without additional power.

Active indicators can include lights, light emitting diodes (LEDs), video screens, speakers, or buzzers. Active indicators have the disadvantage of continuing to use power over time, but they can allow host status to be more readily determined in a wide variety of ambient conditions. For example, an active indicator may illuminate a green light to indicate that its battery is healthy, or a red light when its battery needs replacement. This repeated illumination of a light requires power, but may be much more likely to catch the attention of a user than a passive indicator would. This may be particularly true if the device is stored in a dark or low-visibility environment.

For battery powered, standby devices, such as AEDs, conservation of battery power is an important design goal. Such systems that use active status indicators have the additional challenge of reducing the amount of power they expend operating the status indicators. Since these devices may be stored, in standby mode, in a variety of environments there are times when the power used for status indication is excessive. For example, if a status light is designed to be bright enough to be seen in a well lit room, it may be much brighter than necessary when in a dark room or when stored in a cabinet, carrying case or car trunk.

Similarly for an aural status indicator, if the volume level of the indicator has adequate magnitude for a noisy environment, such magnitude may be much higher than necessary in a quiet room setting and therefore consume more power than necessary.

In addition to the problems associated with status indicators of an AED and an AED surrounding operating environment, other problems of active status indicators include the following: An AED operator may have no way of knowing, on an absolute scale, how much battery life is left or remains for a particular AED. Thus, an AED operator might send an AED with a flashing green active status indicator back into service, without knowing that the battery may be on the verge of failure.

Another problem with active status indicators, such as those which include lights, is that a periodic flashing light indicator may be difficult to notice by an AED operator or maintenance person if the ambient environment is brightly lit, such as when an AED is positioned within sunlight. For this reason, some existing AEDs periodically use aural active status indicators and may periodically chirp when the battery level is low. Because chirping can quickly drain a battery, current AED designs attempt to minimize chirping by emitting brief, infrequent, single chirps when the battery level is low. However, such a chirping pattern can be difficult to perceive by an AED operator or maintenance person.

For example, a typical conventional AED with an active status indicator may emit one chirp every five minutes to indicate battery failure or a potential for battery failure. A problem with this approach is that the chirp may be hard to notice and even harder to pinpoint, especially if an AED operator or maintenance person in the surrounding environment are focused on other tasks (e.g., workers in an office). By the time such individuals even discover that there has been a noise, the AED may become silent again due to its frequency of one chirp for every ten minutes. However, more frequent chirping is usually undesirable too because it can drain the dying battery of an AED even more quickly.

Thus, there is a need for an AED active status indicator that is easy to notice and to interpret, yet also conserves remaining battery power. There is also a need for an AED active status indicator with these properties that does not unduly drain the AED battery. There is also a need for status indicators that may sense their operating environment and then adjust accordingly either, or both, indicator intensity or indication event frequency.

SUMMARY OF THE INVENTION

The inventive active status indicator (ASI) system can indicate a status of a host device while the host device is in a non-operative state. The inventive ASI system may have two inventive main features: (1) The status alerts of the host device produced by the inventive ASI system can be more meaningful or unique relative to status alerts provided by conventional ASIs; (2) the inventive ASI system may automatically adjust indicators in response to sensing environmental conditions of the host device.

First Main Feature: Meaningful/Effective Status Alerts Produced by Inventive ASI System According to one exemplary embodiment, the ASI system can determine, or a predetermined value may be provided for, the duration of audible alerts and the amount of delays between the audible alerts based on the condition of a battery of a portable AED. The duration of the audible alerts and amount of delay between the audible alerts may be designed to attract more human intervention relative to conventional alerts.

That is, the inventive ASI system can provide an audio alarm or alert that is more easily noticed, but that does not drain the battery more quickly than conventional audio alarms in AEDs. One aspect of the inventive ASI system is the realization that a brief, infrequent single chirp can be difficult for humans to notice and to pinpoint or locate. Thus, inventive ASI system can provide a more noticeable chirping pattern that involves rapid, repeated chirping over a brief period (also referred to as an activation window) followed by longer intervals of silence.

For example, the length and number of sounds or "chirps" of an AED may be extended relative to conventional, intermittent sounds of conventional AEDs. As a more specific example, while a conventional AED might chirp once every five minutes, an AED according to the invention might chirp once every five seconds for an alert activation window of thirty seconds and then remain silent for another twenty-nine and one-half minutes.

Even though twelve chirps are emitted per hour in both scenarios, the rapid chirp pattern during the thirty second length alert activation window according to the invention may be more noticeable by people in the vicinity of the AED. The inventors have discovered that the rapid chirping pattern during an alarm activation window, such as the thirty-second length window noted above, can get the attention of a user and allow the user to determine the location of the AED which may need servicing. Thus, the alert or alarm of the inventive ASI system may be more effective compared to conventional AEDs with ASIs which do not have the inventive pattern described herein.

The inventive ASI system may also determine, or predetermined values may be provided for, an optimal frequency and/or pattern of the alert activation windows over a twenty four hour period. As noted above, the alert activation window may describe when the ASI system generates an alert such as a chirp sound for a predetermined period of time with a predetermined frequency. The inventive ASI system can schedule, or a predetermined schedule can be provided for, the alert activation windows so that the windows are spaced evenly over a twenty four hour period or the ASI system can take on many different approaches, such as a statistical approach on the number and pattern of the windows during any twenty four hour period.

The inventive ASI system may determine, or predetermined values may be provided for, the frequency and pattern of the alert activation windows by assessing a combination of the environment of the AED, time of day, day of the week, and work schedules of employees of a given location. For example, the inventive ASI system may schedule, or predetermined values may be provided for, alert activation windows only during the operating hours of a given AED environment. In a typical office setting, hours of operation in which most humans would normally be present are usually between 9 AM and 5 PM. The inventive ASI can schedule, or may be provided with predetermined values for, alert activation windows that occur only during these hours of operation since it is likely that alert activation windows would not be noticed by people outside of the hours of operation of a typical office setting.

This inventive ASI system also can provide, or can be provided with predetermined values to activate, multiple, different audible patterns to convey additional information. For example, the rhythm of a chirp pattern or the chirp pitch (or both) or different noises such as chirping and buzzing can be varied to convey a variety of information such as battery level, pad status, hardware status, software status and the like. Further, to indicate severe conditions such as failure of an AED, instead of an audible sound like a chirp, the inventive ASI system could use a voice synthesizer to generate speech with a message to convey failure of an AED. Moreover, visual devices, such as LEDs, be used in conjunction with audible alerts to provide a wide range of low power status indicator possibilities.

According to one exemplary embodiment of the invention, the inventive ASI system can employ visual indicators with a variety of flashing patterns. For example, an AED having a visual status indicator according to the invention might quickly flash three times in succession when the battery level is high, twice if the battery level is around 50%, and only once if the battery level is low. In this way, a maintenance person can determine at a glance, not just whether the battery is still capable of providing a therapeutic electric shock, but also how much battery life is left.

Moreover, different combination of colors and/or flashing patterns can be used to convey additional information. For example, while one or more colors may be used for indicating battery life, a different set of colors may be used to indicate the status of other aspects of the AED, including pad status, software status, hardware status, and the like.

Second Main Feature: Environmental Sensing by Inventive ASI System

The operation of the ASI system may automatically adjust indicators in response to sensing environmental conditions of the host device while the host device is in the non-operative state. A non-operative state of the host device usually includes situations in which the host device is performing less than all of its primary functions. For example, a non-operative state for automatic external defibrillators (AEDs) usually includes situations in which an AED is not performing a rescue on a patient. Functions that may occur during non-operative states in AEDs may include self-tests and active status indicator events.

The inventive ASI system may supply status information about the host device to a user. When the host device is operational, the ASI system may also supply the host device with environmental conditions sensed by the ASI system. The host device can query the ASI system for these parameters when the host device is in an operational state.

While the host device is in the non-operative state, the inventive ASI system can adjust the intensity level, duration of powering, or duration between powering, or any combination thereof, for status indication. These adjustments can reduce power consumed by the ASI system. Battery operated devices with long stand-by requirements, such as an automatic external defibrillator (AED), may benefit from increased battery life because of power conserving features of the inventive ASI system.

The inventive ASI system may also operate in a low power standby or sleep mode while the host device is also in a standby mode. However, the low power standby mode of the ASI system is different from the standby mode of the host device in that the ASI system can be "awakened" from its standby mode. Meanwhile, the host device becomes fully operational when it is switched from its standby mode or "off" mode.

The inventive ASI system can indicate the status of a host device by using illuminated indicators, indicator lights, audible speakers, or other outputs to a user. The intensity level of the indicator can be automatically adjusted to one that is appropriate for the environment. The inventive system can use light sensors, microphones, or other sensors to detect the environment and adjust the indicator accordingly. For example, the inventive ASI system may sense that a room is dark and then lower the brightness of an indicator light. In a brighter room, the inventive ASI system may increase the intensity of an indicator light so that it can still be seen.

In the case of an audible indicator, the inventive ASI system may sense the noise level in the room and then adjust the volume of the audible indicator output as needed. Supplying only the level of indication that a situation requires, may consume considerably less power than always supplying the maximum level of indication. This power savings can extend the battery life of battery-operated host devices.

The inventive ASI system may change the delay between indicator events in response to the environment. For example, if the room is extremely quiet, there might not be anyone present to see or hear an indicator event. Thus, the ASI may reduce power consumption by illuminating a light or chirping a speaker less frequently. Each illumination of the light or sounding of a speaker may be referred to as an indicator event.

The inventive ASI system may detect when the host device is enclosed, such as in a case, cabinet or car trunk and use this information to reduce the intensity or frequency of the status indicators. The ASI may cease indicator functions entirely in such environments. For host devices that are stored away until needed, this ASI functionality may significantly extend battery life. A common example of such a situation is an AED enclosed in a non-transparent or opaque, hard case where it is readily accessible during an emergency.

The inventive ASI system may detect when the host device is enclosed using a switch or magnetic detector. As an example of a magnetic detector, a reed switch in the host device may align with a magnet affixed to the case or enclosure. This can indicate to the inventive ASI system that the host device is in a specific environmental situation and indicator outputs should be adjusted accordingly. For example, if the host device is stored in an opaque carrying case, there may be no need to illuminate any indicator lights. Ceasing or reducing indicator events which might be unnecessary can significantly extend battery life of the host device.

The inventive ASI system may use reflections to detect when the host device is enclosed. If a large enough percentage of the light emitting from an indicator light of the host device is reflected right back into the light sensor of the host device, there may be a high likelihood that a cabinet or enclosure wall just outside the host device is providing a reflective surface. This capability may be used by the inventive ASI system to reduce or cease the indicator events and thus conserve power.

In addition to reacting to environmental conditions, the inventive ASI system may also adjust indicators in response to internal events of the host device. The ASI system may reduce indicator intensity levels, duration of powering for an indicator, and increase delays between indicator events if a battery level of the host device is below a certain threshold. In such situations, the host device can detect low battery power status during normal operations and set a flag that can be checked by the ASI system. The ASI can adjust indicator operations in response to this flag in order to prevent rapid discharge of the remaining battery power.

The inventive ASI system, according to another exemplary aspect, may not detect environmental conditions every time a status indicating event is scheduled to occur. That is, the inventive ASI system can detect environmental conditions such as ambient light conditions or ambient acoustic noise conditions at a rate that can be different than a rate set for an indicating event.

Various aspects of the present invention may be more clearly understood and appreciated from a review of the following detailed description of the disclosed embodiments and by reference to the drawings and the claims that follow. Moreover, other aspects, systems, methods, features, advantages, and objects of the present invention will become apparent to one with skill in the art upon examination of the following drawings and detailed description. It is intended that all such aspects, systems, methods, features, advantages, and objects are included within this description, are within the scope of the present invention, and are protected by the accompanying claims.

BRIEF DESCRIPTION OF THE DRAWINGS

FIG. 13A is a logic flow diagram illustrating an exemplary routine for sensing the environment in a system with a visual ASI that is environmentally responsive according to one exemplary embodiment of the invention.

FIG. 13B is a logic flow diagram illustrating an exemplary routine for sensing the environment in a system with an auditory ASI that is environmentally responsive according to one exemplary embodiment of the invention.

FIG. 14A is a logic flow diagram illustrating an exemplary routine for setting the indicator intensity and frequency in a system with a visual ASI that is environmentally responsive according to one exemplary embodiment of the invention.

FIG. 14B is a logic flow diagram illustrating an exemplary routine for setting the indicator intensity and frequency in a system with an auditory ASI that is environmentally responsive according to one exemplary embodiment of the invention.

DETAILED DESCRIPTION OF EXEMPLARY EMBODIMENTS

The inventive ASI system can determine, or predetermined values may be provided for, the duration of audible or visual alerts or both and the amount of delays between the alerts based on the condition of an element of a portable AED, such as a battery. The duration of the audible alerts and amount of delay between the audible alerts may be designed to attract more human intervention relative to conventional alerts.

The inventive ASI system may also comprise an active status indicator (ASI) whose operation is automatically adjusted in response to its environment while the host device is in a non-operative state. The inventive ASI system may supply status information about a host device to a user while the host device is in a non-operative state. The inventive ASI system may adjust the intensity level, duration of powering, or duration between powering of any status indication in response to the ambient environment of the host system. Such adjustments may reduce power consumed by the ASI system thereby extending battery life of the ASI system and the host device.

The inventive ASI system may indicate the status of a host device using illuminated indicators, indicator lights, audible speakers, or other outputs to a user. The intensity level, dura- tion of powering, or duration between powering, or any combination thereof, of the indicators may be automatically adjusted to one that is appropriate for the environment and that may also attract more human intervention is that is desired based on the condition of an element, like a battery, of AED.

The inventive system may comprise an ASI processor which may comprise a microcontroller with a low-power sleep mode for sensing the environment and controlling the active status indicators accordingly. The inventive ASI system is designed to substantially minimize or eliminate all activity and power consumption during its sleep mode. The ASI processor may also be used to support other functions of the host system such as an on/off switch response, self test operations, or controlling the operational state of the host systems main processor.

Figure 1:
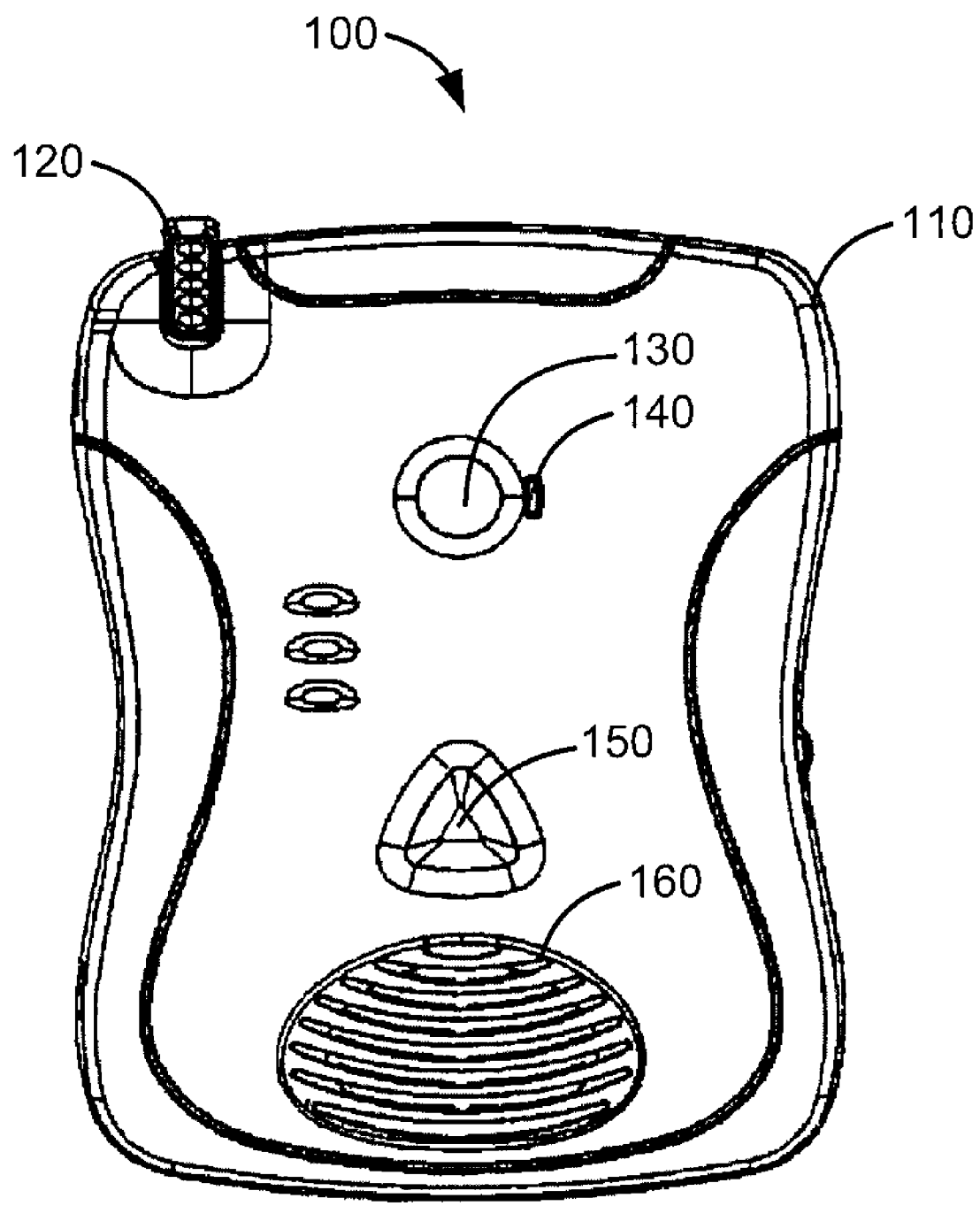
FIG. 1 illustrates a plan view of an AED according to one exemplary embodiment of the invention.

Turning now to the drawings, in which like reference numerals refer to like elements, FIG. 1 illustrates a plan view of an AED 100 with an environmentally responsive ASI system according to one exemplary embodiment of the invention. Even while AED 100 is in standby mode, light-pipe 140 can be illuminated by LED 235 (see FIG. 2) which may serve as an active status indicator (ASI) for AED 100.

Speaker 160 may also provide active status indication. Additionally, speaker 160 may provide synthesized speech instructions or other audible information such as alerts that may include, but are not limited to, sounds, like chirps and buzzes, and the like. Connector 120 can connect patient electrodes (see FIG. 1) to AED 100.

Patient electrodes (not illustrated in FIG. 1 but see FIG. 5) can be used to monitor ECG information from a patient to determine if the patient's cardiac rhythm is suitable for defibrillation shock. If so, the operator may be instructed to press button 150 to initiate an electrical shock through the patient electrodes attached at connector 120. The outer housing 110 of AED 100 may contain and protect the electronic components of AED 100 including ASI circuit 200 (see FIG. 2).

An on/off button 130 can be used to power AED 100 into an operational mode or transition AED 100 into standby mode. While the on/off button 130 appears to the user to turn off AED 100 completely, the on/off button 130 may actually turn off power to a host processor 410 (See FIG. 4) while placing an ASI processor 210 (See FIG. 4) into its very low power sleep mode or standby mode.

Figure 2:
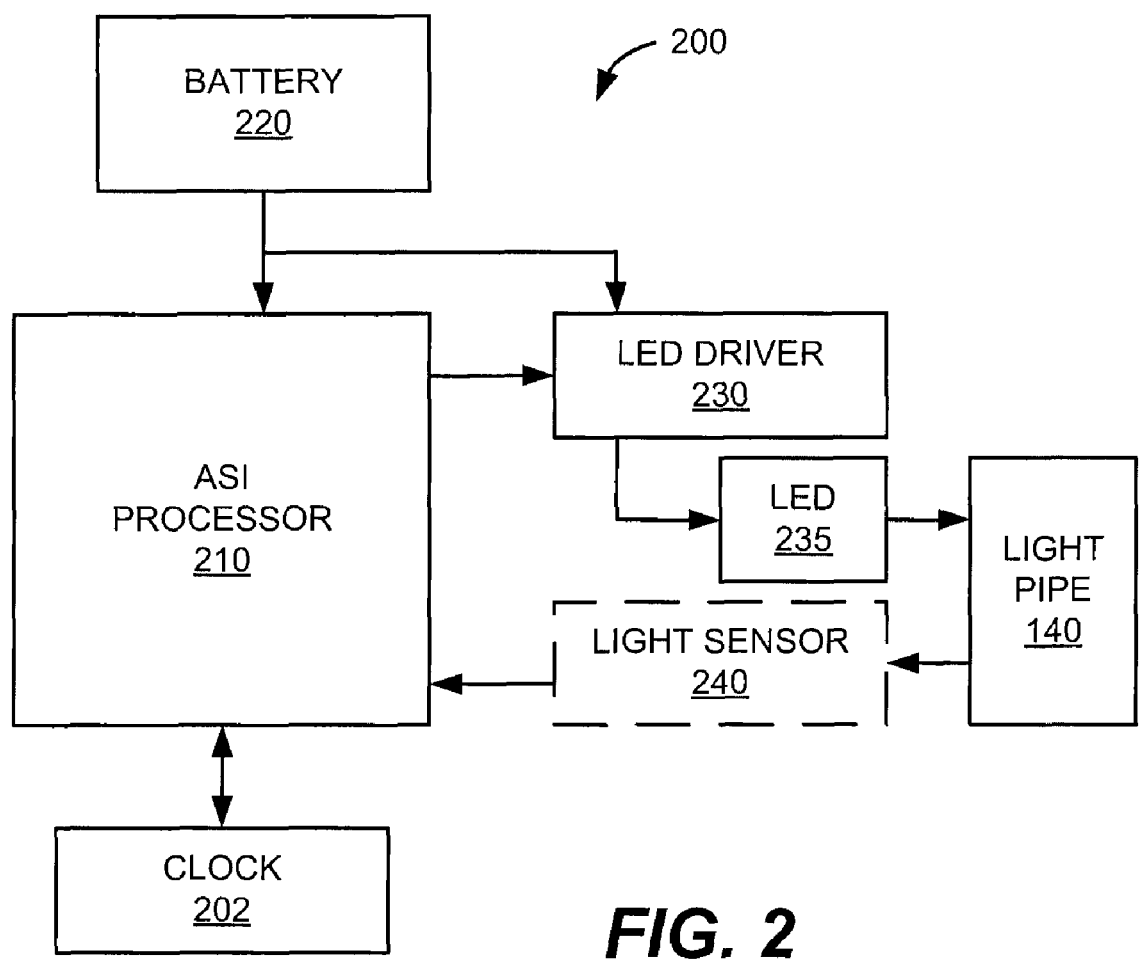
FIG. 2 is a functional block diagram illustrating the ASI processor and an environmentally responsive LED indicator according to one exemplary embodiment of the invention.

Referring now to FIG. 2 which illustrates a functional block diagram of an effective alert generating and environmentally responsive ASI circuit 200A according to one exemplary embodiment of the invention, an LED light 235 can be used as an active visual indicator. ASI processor 210 may comprise a general processor such as the MSP430F1232, an ultra-low-power microcontroller, made by Texas Instruments. However, one of ordinary skill in the art will appreciate that ASI processor 210 may comprise a microcontroller, microprocessor, DSP processor, application specific logic, programmable logic, or numerous other forms without departing from the spirit and scope of the invention. Battery 220 powers the ASI circuit 200.

The ASI processor 210 may be coupled to a clock 202 which can provide timing signals to the ASI processor 210. The clock 202 can also track time in various increments such as seconds, hours, weeks, days, months, and years. The clock 202 may be part of the ASI processor, however, it has been illustrated as a separate component in FIG. 2.

The ASI processor 210 may spend most of the time in a low-power sleep mode. The clock 202, which can include timers, may wake the ASI processor 210 at certain time intervals, such as every few seconds, or according to a predetermined schedule to allow it to briefly illuminate LED 235 thereby providing a status indication.

Prior to illuminating LED 235, ASI processor 210 can sample a light sensor 240 to determine the ambient light level around the host device. The light sensor 240 can comprise a photodiode. However, other light sensors besides photodiodes are not beyond the scope of the invention. The light sensor 240 is illustrated with dashed lines to indicate that it is an optional component of the system and may not be included in certain exemplary embodiments of the invention.

LED driver 230 can control the intensity, or brightness, level of LED 235. LED driver 230 may control this intensity using a pulse width modulation (PWM) technique when driving LED 235. ASI Processor 210 sets this intensity level based on ambient light levels sampled from sensor 240.

Light pipe 140 may be a translucent plastic element that optically couples LED 235 and light sensor 240 to the outside of system housing 110. An exemplary application of the inventive ASI system can comprise the periodic illumination of LED 235 in a green state to indicate that the host system is operating properly and further comprise changing the illumination state of LED 235 to red if the host system requires operator attention. Operator attention may be required, for example, because of a failed internal self test or a low charge detected from the battery 220.

The ASI processor 235 can also determine the duration of the visual alerts produced by LED 235 and the amount of delays between the visual alerts based on the condition of an element of the portable AED 100, such as a condition of the battery 220. The duration of the visual alerts and amount of delay between the visual alerts may be designed to attract more human intervention relative to conventional alerts. Further details of the visual alerts produced by the ASI processor 210 will be discussed below in connection with FIG. 12.

Figure 3:
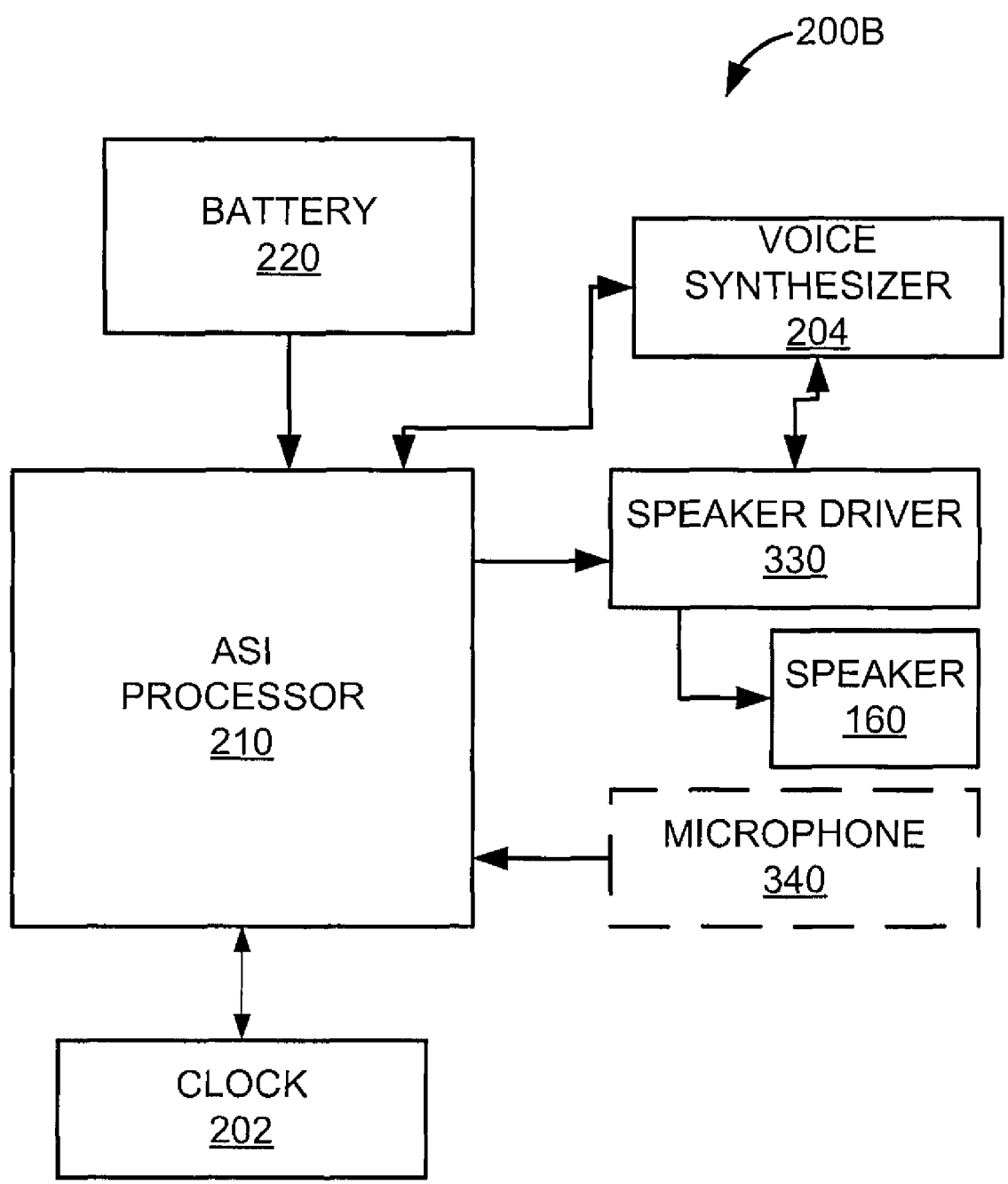
FIG. 3 is a functional block diagram illustrating the ASI processor and an environmentally responsive audible indicator according to one exemplary embodiment of the invention.

Referring now to FIG. 3, which illustrates a functional block diagram of an effective alert generating and environmentally responsive ASI circuit 200B according to one exemplary embodiment of the invention, sound from a speaker 160 is used as an active, aural indicator. Battery 220 powers the ASI circuit 200. ASI processor 210 may spend most of the time in a low-power sleep mode. Clock 202, which may be internal to the ASI processor 210 but has been illustrated as external relative to the ASI processor 210, can wake processor 210 every few seconds to allow it to sound the speaker 160 thereby providing a status indication.

Prior to sounding speaker 160, the ASI processor 210 can sample a microphone 340 to determine the ambient noise level around the host device. The microphone 340 is illustrated with dashed lines to indicate that it is an optional component of the system and may not be included in certain exemplary embodiments of the invention.

Speaker driver 330 that is coupled to the speaker 160 can control the volume, or loudness, of speaker 160. The ASI Processor 210 can set this volume level based on ambient noise levels sampled from microphone 340.

The ASI Processor 210 and speaker driver 330 may also be coupled to an optional voice synthesizer 204. The voice synthesizer 204 can be used by the ASI processor 210 to generate human perceptible speech, such as for alerts like a fault condition when a battery failure will soon occur. The voice synthesizer 204 is illustrated with dashed lines to indicate that it is an optional component of the system and may not be included in certain exemplary embodiments of the invention.

The ASI processor 210 can determine, or predetermined values may be provided to the ASI processor 210 for, the duration of the audible alerts produced by speaker 160 and the amount of delays between the audible alerts based on the condition of an element of the portable AED 100, such as a condition of the battery 220. The duration of the audible alerts and amount of delay between the audible alerts may be designed to attract more human intervention relative to conventional alerts. Further details of the audible alerts controlled by the ASI processor 210 will be discussed below in connection with FIG. 10.

Figure 4:
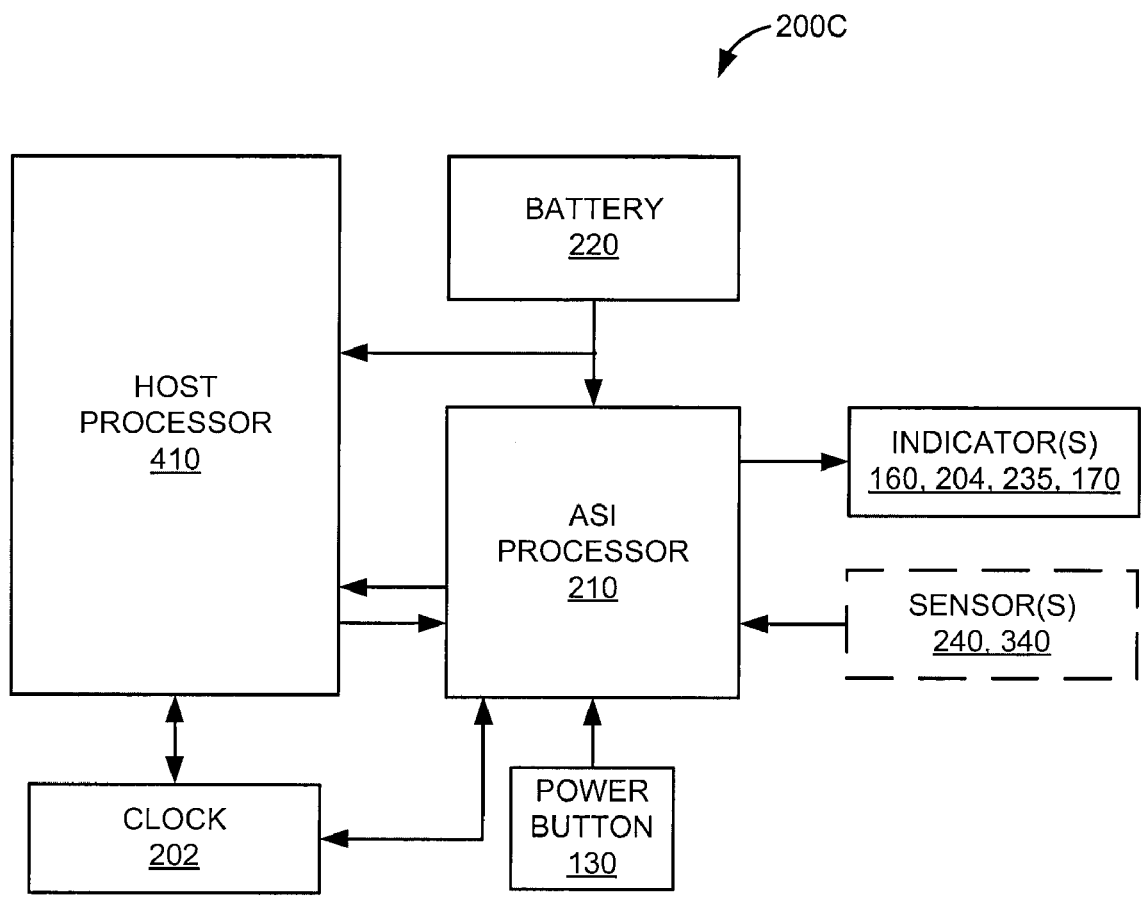
FIG. 4 is a functional block diagram illustrating the relationship between the ASI processor and the host processor according to one exemplary embodiment of the invention.

Referring now to FIG. 4 which illustrates a functional block diagram 200C illustrating a relationship between ASI processor 210 and a host processor 410 of an AED 100. Battery 220 powers the system 200C, including both processors 210 and 410. ASI processor 210, which may spend most of the time in a low-power sleep mode, may wake every few seconds to sample sensors that can include the light sensor 240 and the microphone 340 as well as actuate active status indicators that can include the LED 235 and the speaker 160.

ASI processor 210 may also wake periodically to perform, or cause to be performed, built in self tests of the host system. Based on these self tests, the ASI processor 210 can detect a fault condition or preventive maintenance condition for the AED 100. For example, the ASI processor 210 can detect a preventive maintenance condition, such a low battery condition based on its self tests. The ASI processor 210 may activate indicators such as the speaker 160 or LED 235 or a display 170 (illustrated in FIG. 5) or any combination thereof. The ASI processor 210 may also monitor power button 130 in order to turn host processor 410 on and off.

The ASI processor 210 may also wake periodically based on a scheduled alert that the ASI processor 210 calculated based on a previous self test or based on predetermined values coded into the ASI processor 210. That is, at a first instance of time, the ASI processor 210 may run a self test to determine a status of the battery 220. Based on this self test, the ASI processor 210 may determine that the battery is running low but may still be able to power the AED 100 if use of the AED 100 is needed by an operator.

Therefore, the ASI processor 210 can generate a schedule for itself to way up at certain future instances of time to indicate this condition of the battery. Alternatively, the ASI processor 210 may access a predetermined schedule that is already coded into the ASI processor 210 or a neighboring memory storage device. The ASI processor 210 can be designed such that it does not need to run the battery self test again until some human interaction has occurred. In this way, battery life is further preserved by the ASI processor 210 without running any unnecessary self tests if there has been no human interaction since a previous self test. Further details of the schedule for alerts generated or accessed by the ASI processor 210 will be discussed below in connection with FIGS. 10-11.

Figure 5:
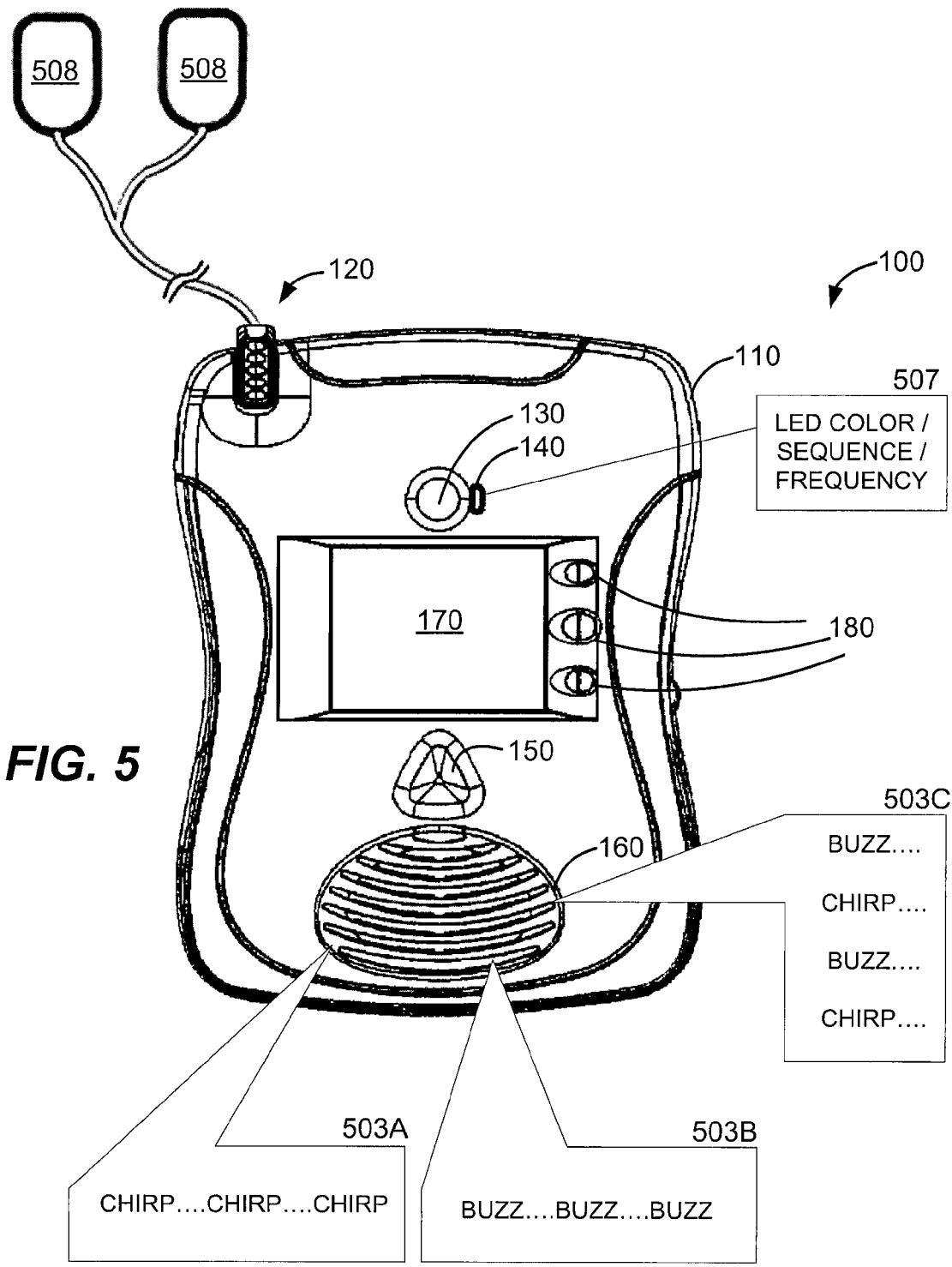
FIG. 5 illustrates a plan view of an AED sounding different audible alerts and illuminating different visual alerts according to one exemplary embodiment of the invention.

Referring now to FIG. 5, this figure illustrates a plan view of an AED 100 sounding different audible alerts 503A, 503B, 503C and illuminating different visual alerts 507, such as light pipe 140 from LED 235 or visual display 170, according to one exemplary embodiment of the invention. The first audible alert 503A may comprise a series of "chirp" sounds produced by the speaker 160. This first audible alert 503A may be designed to indicate a condition of a specific element of the AED 100, such as for the battery 220.

The second audible alert 503B may be designed to indicate a condition of a specific element of the AED 100 that is different from the one designed for the first alert 503A. The second audible alert 503B may comprise a series of "buzzing" noises produced by the speaker 160 and may indicate a condition of another element of the AED 100 besides the battery 220, such as for the electrodes or pads 508 of the AED 100.

The third audible alert 503C may be may be designed to indicate a condition of a specific element of the AED 100 that is different from the first alert 503A and second alert 503B. The third audible alert 503B may comprise a series of alternating "chirp" and "buzzing" noises produced by the speaker 160 and may indicate a condition of another element of the AED 100 besides the battery 220 and pads 508, such as for the hardware or software of the AED 100. Alternatively, the series of alternating "chirp" and "buzzing" noises may indicate that both the battery 220 and pads need changing or maintenance.

In addition to different audible alerts 503 to indicate various conditions of elements of the AED 100, the AED 100 may also produce various combinations of visual alerts 507 to indicate various conditions of the AED 100. For example, the visual alerts 507 can comprise different colored LEDs 235 that illuminate light pipe 140 to indicate conditions of different elements of an AED 100. For example, a flashing red colored LED 235 can indicate a low battery 220 condition. The frequency of the illumination of the red colored LED 235 can be increased to indicate different conditions of the battery 220.

For example, a slow blinking red colored LED 235 may indicate that the battery 220 can power the LED for a shock treatment, but the number of shocks that may be administered may be limited. A fast blinking red colored LED 235 may indicate that the battery is very close to complete failure or depletion of its charge. A constant red colored LED 235 that is illuminated can indicate complete battery failure.

Similar to the red colored LED 235 that may indicate a condition of the battery 220, a yellow colored LED 235 can indicate a condition of the pads or electrodes 508 of the AED 100. A slow flashing yellow colored LED 235 can indicate that the pads 508 can be used but should be changed. A fast flashing colored LED 235 can indicate that the pads 508 can be used but only a few or a single use may remain before they fail. A constant yellow colored LED 234 that is illuminated may indicate that the pads have failed and cannot be used to administer a shock.

Alternate flashes of a red colored LED 235 and a yellow colored LED 235 can indicate a condition of another element of the AED 100 besides the battery 220 and the pads 508, such as for the hardware or software of the AED 100. Alternatively, the alternating colors of red and yellow colored LEDs 235 that are illuminated may indicate two separate conditions, such as for the pads 508 and battery 220.

The ASI processor 210 can also display text or visual graphics on display 170 to indicate a condition. For example, the ASI processor 210 can have a graphic displayed on display 170 that shows a flashing battery and that displays text such as, "Replace Battery!" To obtain more details of a particular alert generated on display 170, an operator may manipulate buttons 180 to request further information or to input information into the AED as will be described below.

The invention is not limited to the number, type, frequency, and combination of visual and aural alerts described above. Other combinations of alerts with various colored LEDs 235 and various types of audible alerts produced by the speaker 160 are not beyond the scope of the invention.

Figure 6:
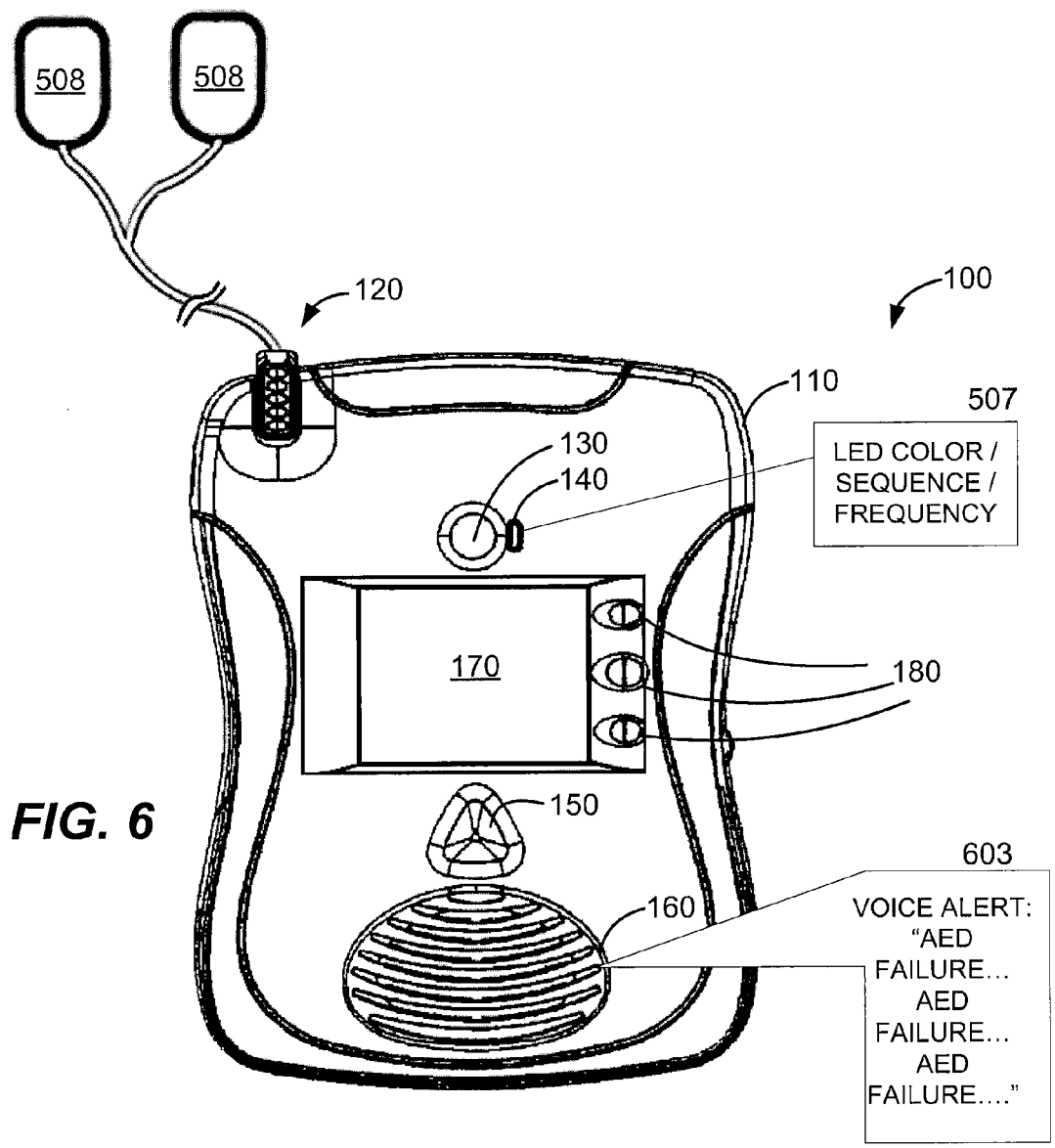
FIG. 6 illustrates a plan view of an AED sounding an audible voice synthesized alert and illuminating different visual alerts according to one exemplary embodiment of the invention.

FIG. 6 illustrates a plan view of an AED 100 sounding an audible voice synthesized alert 603 and illuminating different visual alerts 507 according to one exemplary embodiment of the invention. In this exemplary embodiment, the ASI processor 210 can produce a voice alert 603 by using the voice synthesizer 204. Since the voice synthesizer 204 may consume more power than simple alert sounds, such as alerts 503 of FIG. 5, the ASI processor 210 may reserve the use of voice synthesized alerts 603 for only severe alert conditions of the AED 100. The ASI processor 210 may only use voice synthesized alerts sparingly and based on a calculated probability that a human operator may be in the vicinity of the AED 100.

For example, if the AED 100 is experiencing a severe condition, such as a complete failure of a component or element, like failure of the defibrillator system or failure of hardware or software, the AED 100 can produce a voice alert 603 to indicate this severe condition which will likely be more noticeable than simple sounds 503, such as those described above in connection with FIG. 5. The ASI processor 210 may also determine the likelihood that a human operator may be in the vicinity of the AED 100 by basing its decision to produce the voice synthesized alert 603 by assessing various conditions of the environment of the AED 100, such as the work schedule of employees as will be discussed below in connection with FIGS. 7-11. Alternatively, a predetermined schedule associated with different classes of work environments may be accessed by the ASI processor 210. Meanwhile, the visual alerts 507 in FIG. 6 can be the same as those described above in connection with FIG. 5.

Figure 7A:
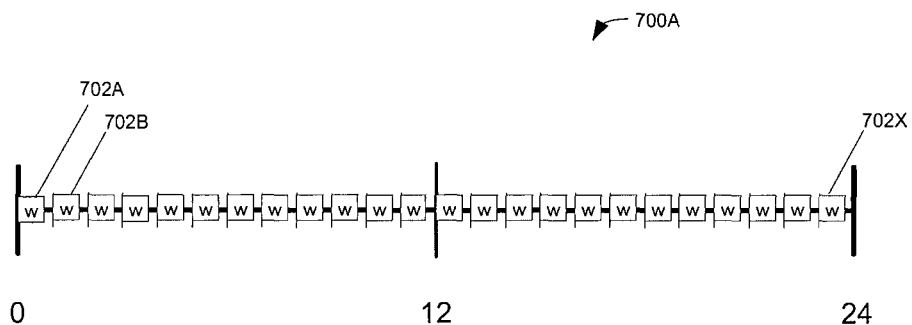
FIG. 7A illustrates a timeline with evenly spaced alarm activation windows over a twenty-four hour period according to one exemplary embodiment of the invention.

Referring now to FIG. 7A, this figure illustrates a timeline 700A with evenly spaced alarm activation windows 702A-X over a twenty-four hour period according to one exemplary embodiment of the invention. It is noted that the size of the alarm activation windows 702 illustrated in the several figures may not be proportionate to their length as described in the text of this detailed description. In other words, the alarm activation windows 702 may not be drawn to scale as illustrated compared to what is described in the text and the windows 702 may have exaggerated or reduced sizes relative to what is described in the text of this section.

It is also noted that the embodiments illustrated in FIGS. 7-8 have alarm activation windows 702 that start on each hour of a twenty-four hour period according to one exemplary embodiment of the invention. According to other exemplary embodiments not illustrated, the alarm activation windows 702 could start on half-hour increments instead of each hour as illustrated in FIGS. 7-8. The invention is not limited to certain start and stop times within any hour of a twenty-four hour period. Other start and stop times not illustrated in FIGS. 7-8 are not beyond the scope of the invention.

Referring back to FIG. 7, the alarm activation windows 702A-X in this exemplary embodiment can start at the beginning of each hour and can have a duration of thirty seconds. As noted above, the clock 202 of the AED 100 can track the seconds, minutes, hours, days, months, and years for the ASI processor 210.

During each activation window 702, the ASI processor 210 can have the speaker 160 chirp once every five seconds for thirty seconds. Then, for the remaining fifty-nine and half minutes of a hour, the speaker 160 can remain silent. However, one of ordinary skill in the art will recognize that other lengths of the alarm activation windows and other timing (such as starting a window at the half of every hour) are not beyond the scope of the invention. For example, the alarm activation windows 702 can be randomly started over any length of a period, such as over a twenty-four hour period, as described below in connection with FIG. 7B.

Figure 7B:
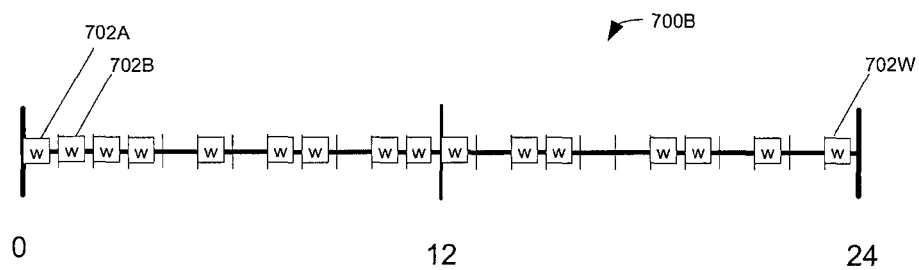
FIG. 7B illustrates a timeline with randomly spaced alarm activation windows over a twenty-four hour period according to one exemplary embodiment of the invention.

Referring now to FIG. 7B, this figure illustrates a timeline 700B with randomly spaced alarm activation windows 702A-X over a twenty-four hour period according to one exemplary embodiment of the invention. The ASI processor 210 according to this exemplary embodiment may use a random number generator or function to determine, or a predetermined random set of values may be accessed for, the magnitude or length of each alarm activation window 702 as well as the starting time for each alarm activation window 702.

Figure 8A:
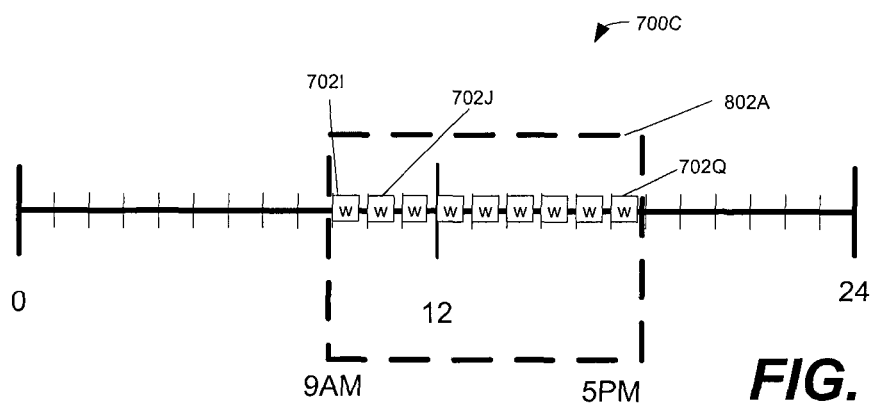
FIG. 8A illustrates a timeline with evenly spaced alarm activation windows that occur between a range of hours within a twenty-four hour period according to one exemplary embodiment of the invention.

Referring now to FIG. 8A, this figure illustrates a timeline 700C with evenly spaced alarm activation windows 702A-H that occur between an optimal range 802A of hours, such as the hours of nine AM to five PM, within a twenty-four hour period according to one exemplary embodiment of the invention. According to this exemplary embodiment, the ASI processor 210 can assess the operating environment of the AED 100. As part of a program executed by the ASI processor 210 or by the host processor 410, an operator of the AED 100 can be prompted to enter the optimal range 802 of work hours or hours in which most people will be in the vicinity of the AED 100 and in which there may be the greatest demand for the AED 100.

For example, in a traditional office setting, an operator of the AED 100 may enter the range 802A of hours of nine AM to five PM, with the days of Monday through Friday. In other non-office settings, like an airport, an operator of the AED 100 may enter the optimal range 802A of hours of seven AM to eleven PM with all seven days being accounted, such as Sunday through Sunday. This means that outside of the optimal range 802B, the ASI processor will not schedule any alarm activation windows 702. One of ordinary skill in the art will appreciate that other combinations of alarm activation windows 702 with various start times within the optimal range 802 of work hours are not beyond the scope of the invention.

Figure 8B:
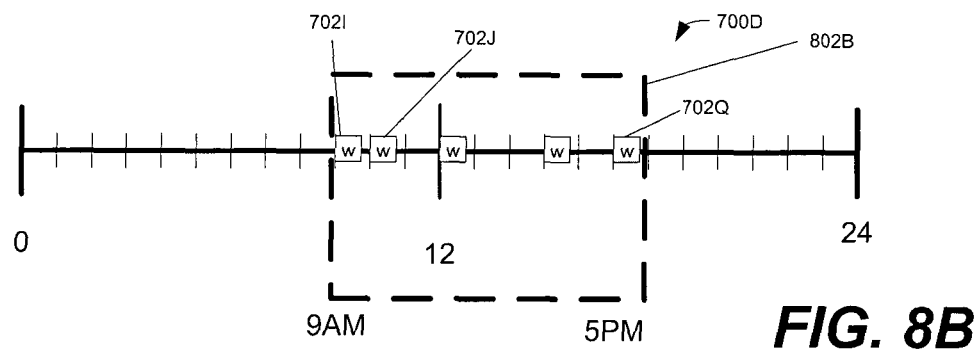
FIG. 8B illustrates a timeline with randomly spaced alarm activation windows that occur between a range of hours within a twenty-four hour period according to one exemplary embodiment of the invention.

Referring now to FIG. 8B, this figure illustrates a timeline 700D with randomly spaced alarm activation windows 702A-H that occur between a predetermined range 802B of hours within a twenty-four hour period according to one exemplary embodiment of the invention. According to this exemplary embodiment, the ASI processor 210 has been provided with information regarding the environment of the AED 100.

Specifically, the ASI processor 210 has been provided with the optimal range 802B working hours of employees who may work adjacent to the AED 100 in a typical office setting. In the exemplary embodiment illustrated in FIG. 8B, the optimal range 802B for the work hours of employees is nine AM to five PM. According to this exemplary embodiment, instead of scheduling alarm activation windows 702 evenly across the optimal range 802B, the ASI processor 210 can randomly schedule the alarm activation windows during the optimal range 802B of working hours. This means that outside of the optimal range 802B, the ASI processor will not schedule any alarm activation windows 702.

Figure 9:
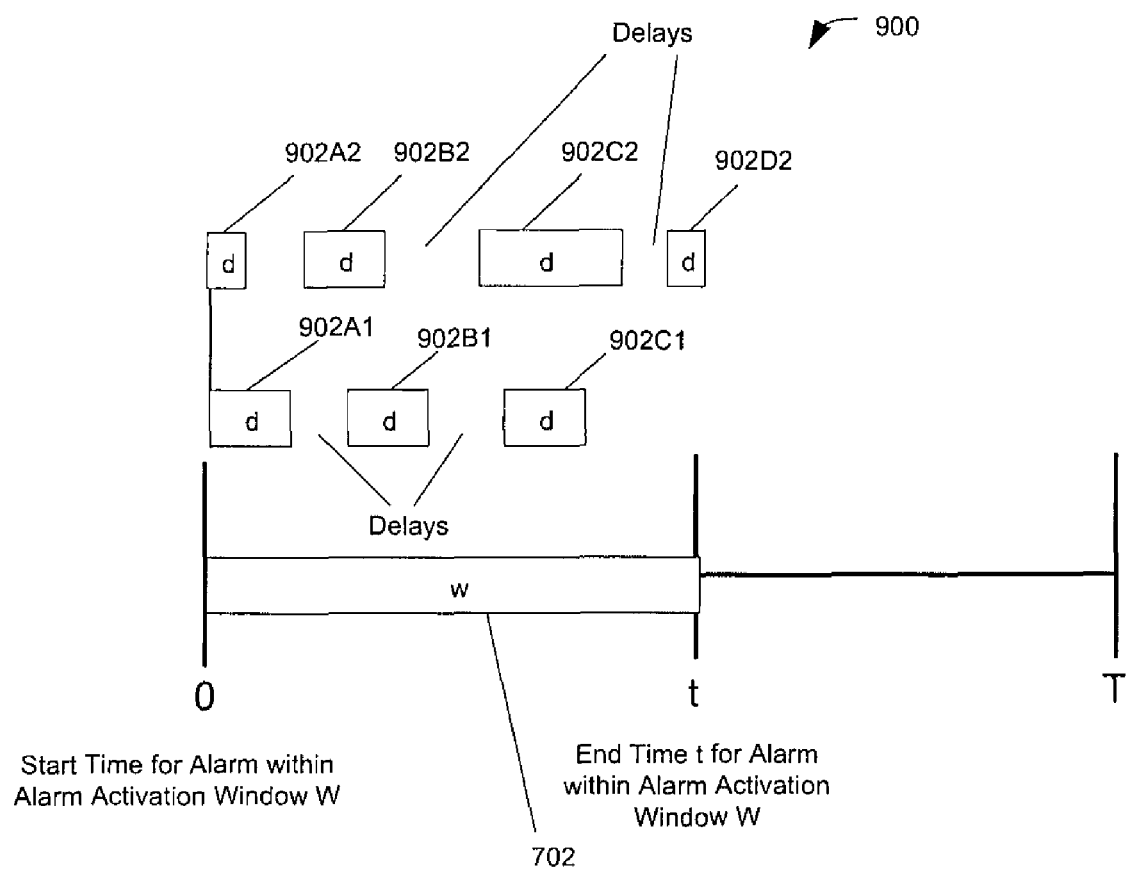
FIG. 9 illustrates the details of alarm activation windows and the duration of alarms according to one exemplary embodiment of the invention.

FIG. 9 illustrates the details of alarm activation windows 702 and the duration 902 of alarms according to one exemplary embodiment of the invention. An alarm activation window 702 comprises a period of time in which the ASI processor 210 may activate one or more alarms or alerts such as producing sounds or voice with the speaker 160 or producing visual alerts such as with the LED 235, or any combination of visual and aural alerts thereof. Each alarm activation window 702 comprises an amount of time defined between a start of a first iteration and an ending of a subsequent iteration of an alarm.

The duration 902 of the alerts or alarms can comprise any length of time within an alarm activation window 702. The duration 902 of each alert within the alarm activation window 702 (for more than one alert or alarm) can be substantially equal or unequal. The duration 902 of each alert can also be random in length as determined by the ASI processor 210 or based on the ASI process 210 accessing a set of random values stored in a memory storage device.

Specifically, the duration of a first set of alerts 902A1, B1, C1 can be equal in length an can be positioned evenly during the alarm activation window 702 as determined by the ASI processor 210 or by predetermined values accessed by the ASI processor 210. In another exemplary embodiment, the duration of a second set of alerts 902A2, B2, C2 can be unequal in length as well as randomly positioned or timed as determined by the ASI processor 210 or as accessed by the ASI processor 210. In this way, the alerts 902 may attract more attention from a human operator compared to alerts of conventional AEDs 100.

Figure 10:
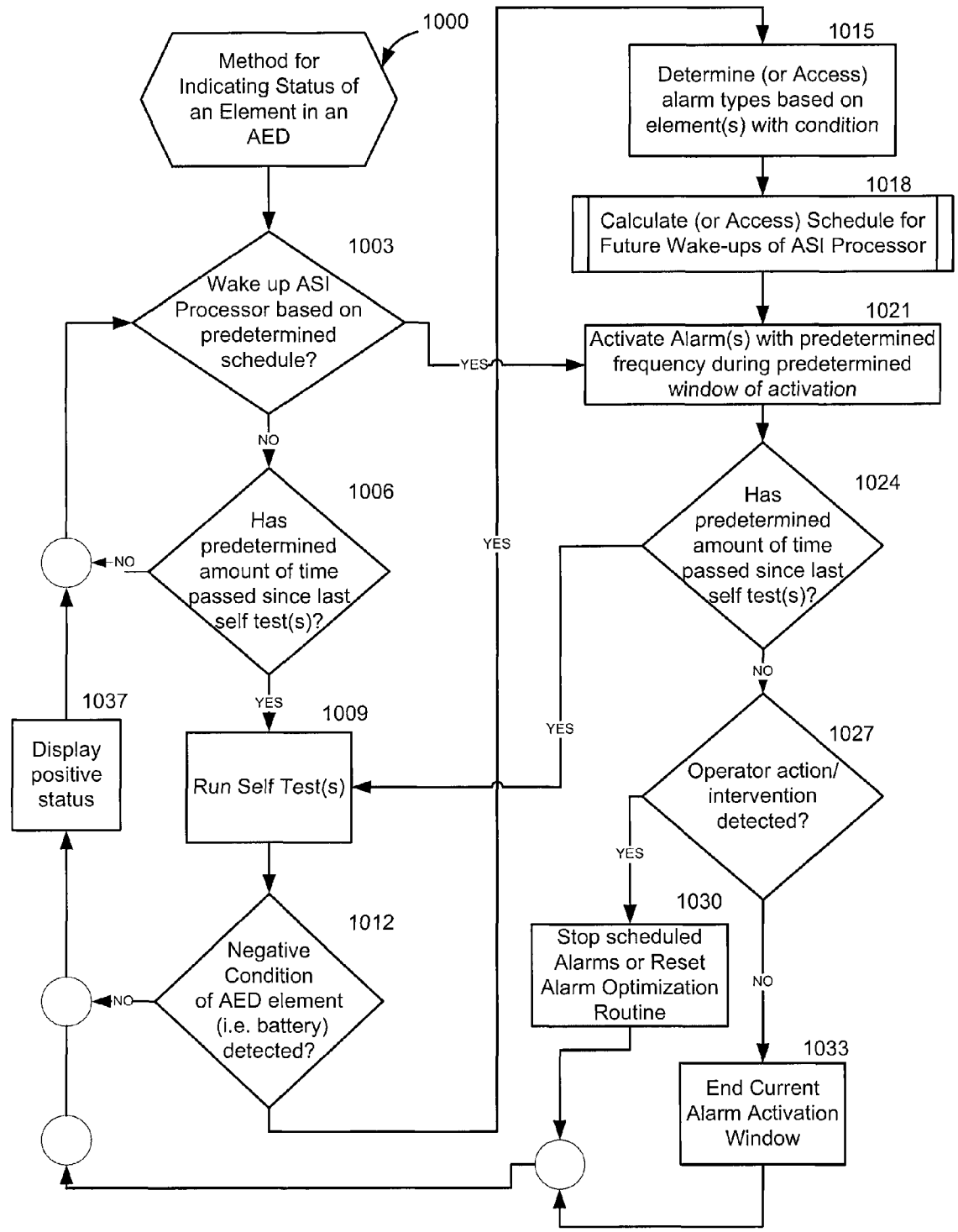
FIG. 10 is a logic flow diagram highlighting exemplary steps for activating an audible alarm with an ASI processor for predetermined alarm activation windows based on a schedule according to one exemplary embodiment of the invention.

Referring now to FIG. 10, this figure is a logic flow diagram highlighting exemplary steps of a method 1000 for activating an audible alarm with an ASI processor 210 for predetermined alarm activation windows 702 based on a schedule according to one exemplary embodiment of the invention. Method 1000 highlights some key functional features of ASI processor 210.

One of ordinary skill in the art will appreciate that process functions or steps performed by the ASI processor 210 may comprise firmware code executing on a microcontroller, microprocessor, or DSP processor; state machines implemented in application specific or programmable logic; or numerous other forms without departing from the spirit and scope of the invention. In other words, the invention may be provided as a computer program which may include a machine-readable medium having stored thereon instructions which may be used to program a computer (or other electronic devices) to perform a process according to the invention.

The machine-readable medium may include, but is not limited to, floppy diskettes, optical disks, CD-ROMs, and magneto-optical disks, ROMs, RAMs, EPROMs, EEPROMs, magnet or optical cards, flash memory, or other type of media/machine-readable medium suitable for storing electronic instructions.

Certain steps in the processes or process flow described in all of the logic flow diagrams referred to below must naturally precede others for the invention to function as described. However, the invention is not limited to the order of the steps described if such order or sequence does not alter the functionality of the present invention. That is, it is recognized that some steps may be performed before, after, or in parallel other steps without departing from the scope and spirit of the present invention.

Additionally, it is recognized that certain steps could be re-arranged in different sequences or entirely deleted without deviating from the scope and spirit of the invention. In other words, it is recognized that the steps illustrated in the flow charts represent one way of achieving a desired result of meaningful alerts for conveying status of elements for an AED. Other ways which may include additional, different steps or the elimination of steps, or the combination of eliminating steps and adding different steps will be apparent to one of ordinary skill in the art.

Further, one of ordinary skill in programming would be able to write such a computer program or identify the appropriate hardware circuits to implement the disclosed invention without difficulty based on the flow charts and associated description in the application text, for example. Therefore, disclosure of a particular set of program code instructions or detailed hardware devices is not considered necessary for an adequate understanding of how to make and use the invention. The inventive functionality of the claimed computer implemented processes will be explained in more detail in the following description in conjunction with the remaining Figures illustrating other process flows.

Referring again to FIG. 10, decision step 1003 is the first step of the process or method 1000 in which it is determined if the ASI processor 210 should be awakened from its standby or inactive state based on a predetermined schedule that it calculated based on previous self-tests that the ASI processor 210 had executed or by a predetermined schedule that is hard coded into the ASI processor 210 or from a predetermined schedule that is accessed by the ASI processor 210. The predetermined schedule may allow the ASI processor 210 to skip executing self tests if the ASI processor 210 knows that an operator has not changed any condition of the AED 100 since the self test for a certain element of the AED 100 was executed. If the inquiry to decision step 1003 is negative, then the "No" branch is followed to decision step 1006. If the inquiry to decision step 1003 is positive, then the "Yes" branch is followed to step 1021.

In decision step 1006, the ASI processor 210 can determine if a predetermined amount of time has passed since the last self test(s) have been run by the ASI processor 210. The ASI processor 210, in addition to scheduling alarm activation windows 702, may also track the time between self tests. This tracking of time between self tests is optional. But such tracking may be beneficial so that the ASI processor 210 will not schedule an alarm activation window 702 if the condition of an element of the AED 100 has changed.

For example, if the ASI processor 210 has scheduled alarm activation windows 702 to alert an operator of a condition for the battery 220, decision step 1006 allows the ASI processor 210 to permit the running of self tests between alarm activation windows 702 in order detect a change in the condition of the battery 220 in case an operator has replaced or repaired the condition of the battery 220 since the last alarm activation window 702.

If the inquiry to decision step 1006 is negative, then the "No" branch is followed back to decision step 1003. If the inquiry to decision step 1006 is positive, then the "Yes" branch is followed to step 1009 in which the ASI processor 210 can run various self tests to determine the conditions of elements of an AED 100. For example, the ASI processor 210 can run self tests to determine the conditions of the battery 220, the pads 508, the hardware, the software, and the defibrillator system of the AED 100.

Next, in decision step 1012, the ASI processor 210 determines if a negative condition of an element of the AED 100 has been detected. For example, in this step, the ASI processor 210 can detect if the battery 220 needs replacement or has a limited number of uses remaining because its voltage or current has dropped below a predetermined level.

Figure 12:
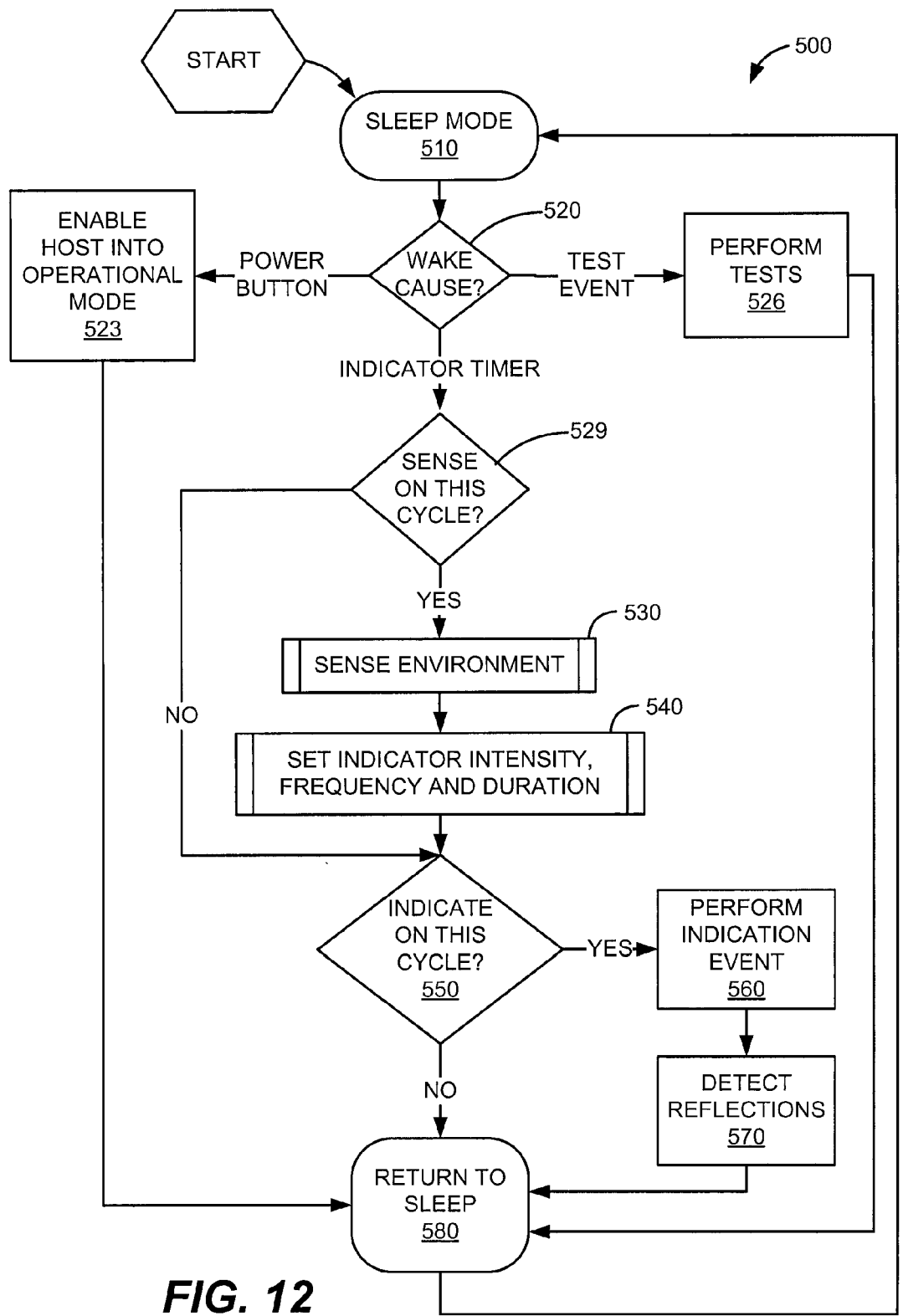
FIG. 12 is a logic flow diagram highlighting exemplary steps for an ASI processor in a system with environmentally responsive active status indicators according to one exemplary embodiment of the invention.

If the inquiry to decision step 1012 is negative, then the "No" branch is followed to step 1037 in which a positive status for one or more AED elements can be conveyed according to routine 540 of FIG. 12. The duration, frequency, and scheduling of the positive status can be determined by the ASI processor 210 or they can be predetermined values that are accessed by the ASI processor 210. The process then proceeds back to decision step 1003.

If the inquiry to decision step 1012 is positive, then the "Yes" branch is followed to step 1015. In step 1015, the ASI processor 210 can determine the types of alarms based on the elements of the AED 100 which need maintenance or repair. The ASI processor 210 can also determine the types of alarms based on the severity of a negative condition detected.

For example, with a battery 220 that could power the AED 100 for a few uses but is not in a critical state of failure, the ASI processor could select a "less" severe alert or alarm such as sounding the speaker 160 with a "chirp" noise 503. If the ASI processor 210 has detected a condition of the battery 220 in which complete failure of the battery is eminent, then the ASI processor 210 could select a voice synthesizer alert 603. Other examples of the types and number of alerts are described above in connection with FIGS. 5-6.

Next in routine 1018, the ASI processor 210 can schedule the alarm activation windows 702 as discussed above in connection with FIGS. 7-9. The ASI processor 210 can take into account the environment of the AED 100 such as the hours of operation in which the most humans may be in the vicinity of the AED 100. As discussed above in connection with FIGS. 7-9, the AED 100 can prompt an operator to input the typical working hours of employees or times in which humans may be in the vicinity of the AED 100 so that the AED 100 schedules alarm activation windows 702 only when humans may be near the AED 100.

Alternatively, the AED 100 can access a predetermined schedule that is associated with a class of environment intended for the AED 100. For example, in a factory or airport environment, the AED 100 may be surrounded by potential users for a duration of twenty-four hours in a day. Similarly, in an office setting, the AED 100 may be surrounded by potential users for only a fraction of twenty-four hours, such as eight hours. Further details of routine 1018 will be discussed below in connection with FIG. 11.

Subsequently, in step 1021, the ASI processor 210 activates one or more alarms or alerts that can be aural or visual or both based on the conditions of the elements of the AED 100 that were detected by the ASI processor 210. These alarms or alerts can have a predetermined frequency and duration for a particular alarm activation window 702 as described above in connection with FIGS. 7-9. As noted above, the frequency of the alarm during an alarm activation window 702 can be constant or random. The schedule for each alarm activation window 702 can be constant or random over a twenty-four hour period or over a course of a week in which the schedule of people who may be in the vicinity of the AED 100 is tracked.

Next, in decision step 1024, the ASI processor 210 can determine if a predetermined amount of time has passed since the last self test(s) have been run by the ASI processor 210. As noted above in connection with decision step 1006, the ASI processor 210, in addition to scheduling alarm activation windows 702, may also track the time between self tests. Step 1024 may be identical to decision step 1006 described above.

If the inquiry to decision step 1024 is positive, then the "Yes" branch is followed back to step 1009 in which the ASI processor 210 can execute one or more self tests. If the inquiry to decision step 1024 is negative, then the "No" branch is followed to decision step 1027 in which the ASI processor 210 can detect if an operator has changed a condition of an element of the AED 100. In this decision step 1024, the ASI processor 210 can sense if a condition of the AED 100 changes.

For example, the ASI processor 210 can detect when the battery 220 has been replaced by sensing a complete removal of power to the AED 100. If this event occurs, then the ASI processor 210 can stop any alerts for the battery 220 or reset its alert schedule for a battery condition such as described in step 1030.

If the inquiry to decision step 1027 is negative, meaning that the ASI processor 210 has not detected any operator intervention based on its alerts, then the "No" branch is followed to step 1033 in which the current activation window 702 is finished. The process then returns to decision step 1003 in which it is determined whether the ASI processor 210 should be awakened from its dormant or stand-by state.

Figure 11:
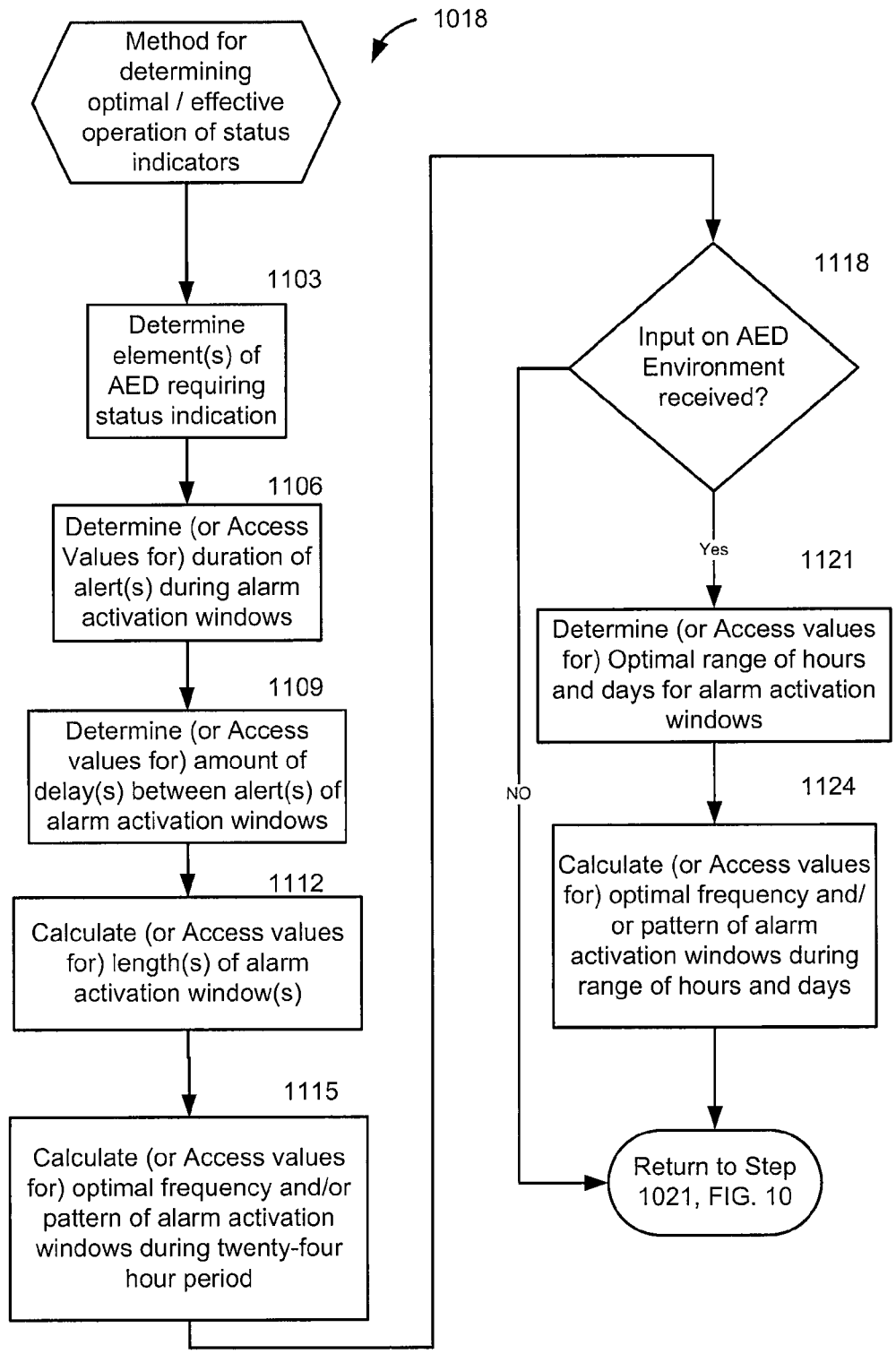
FIG. 11 is a logic flow diagram illustrating exemplary steps for determining optimal operation of an active status indicator, such as an audible alarm for indicating a battery condition, while conserving remaining battery power according to one exemplary embodiment of the invention.

Referring now to FIG. 11, this figure is a logic flow diagram illustrating exemplary steps of a routine 1018 for determining optimal operation of an active status indicator according to one exemplary embodiment of the invention. This routine 1018 is mentioned briefly above in connection with FIG. 10. One operation of an active status indicator can include an audible alarm 503, 603 for indicating a battery condition, while conserving remaining battery power.

Step 1103 is the first step of the routine 1100 in which the ASI processor 210 determines if an element of the AED 100 needs servicing, may be on the verge of failure, or has failed based on data it has collected from self-tests. For example, the ASI processor 210 can determine if a battery 220 needs servicing, if it may be on the verge of failure, or if it has failed based on self tests that may be run by the ASI processor 210 as discussed above in Step 1009 of Figure.

Next, in step 1106, the ASI processor 210 determines, or the ASI processor 210 can access predetermined values for, duration of the alerts within an alarm activation window 702 (see FIGS. 7-9) to attract human attention/intervention based on the severity of the condition that was detected in the one or more self-tests. In this step 1106, the ASI processor 210 can determine, or it can access a predetermined set of values for, how long it should activate an alert that can be visible or heard (or both) by a human operator. The ASI processor 210 can calculate, or it may access predetermined values stored in a memory device for, longer alerts to indicate more severe conditions. Likewise, it can calculate, or the ASI processor 210 may access predetermined values stored in a memory device for, shorter alerts that may indicate less severe conditions. An alert, as defined herein, refers to the length of time that an active status indicator is turned "on" or is active.

Next, in step 1109, the ASI processor 210 can determine, or it may access predetermined values stored in a memory device that correspond to, the amount of delays between alerts within an alarm activation window 702 in order to attract human attention or interaction. Similar to the alert calculation step 1106 described above, the ASI processor 210 can determine, or access predetermined stored values for, how long an indicator should remain inactive or "off" between its active or "on" states within each alarm activation window 702.

In step 1112, the ASI processor 210 can determine, or it may access predetermined values for, the length of the alarm activation windows 702 (see FIGS. 7-9). For less severe conditions of an element of an AED, such as for a battery 220 that can support a few more therapeutic shocks before needing replacement, the ASI processor 210 can calculate, or access predetermined values for, a relatively short alarm activation window 702. Similarly, for a more severe condition, such as a battery 220 on the verge of failure, the ASI processor 210 can calculate, or access predetermined values that translate into, longer alarm activation windows 702.

In step 1115, the ASI processor 210 can calculate, or it may access predetermined values for, an optimal frequency or pattern of the alarm activation windows 702 over a twenty-four hour period. The ASI processor 210 can space alarm activation windows 702 evenly over a twenty-four hour period as illustrated in FIG. 7A or the ASI processor 210 can space the alarm activation windows 702 un-evenly in a non-uniform manner over a twenty-four hour period as illustrated in FIG. 7B. Alternatively, the ASI processor 210 can determine, or predetermined values can be accessed by the ASI processor 210 for, the pattern and/or frequency of the alarm activation windows 702 which are based on mathematical formulas such as by using statistical functions, probability functions, and combinations thereof.

Next, in decision step 1118, it is determined if the ASI processor 210 has been provided any data on the operating environment of the AED 100. In other words, the ASI processor 210 or the host processor 410 (or both) can be provided with a program or software to prompt a user to indicate the operating environment for a particular AED 100. For example, an operator of an AED 100 can be prompted on the normal hours in which most humans will be working in the vicinity of the AED 100, such as the hours for an office environment.

In a typical office setting, a human operator may input the hours of nine AM to five PM as the normal times that it is likely that humans will be in the vicinity of the AED 100 and thus, able to hear or see any active status indicators of the AED 100. Similarly, in a factory environment, a human operator can input the hours of operation in which workers in the factor would be present and adjacent to the AED 100. The invention is not limited to the number and types of environment in which an AED 100 could be deployed and in which various hours of which humans are likely to be adjacent to an AED 100 can be inputted by an operator.

If the inquiry to decision step 1118 is negative, meaning that the AED 100 has not received any input on the conditions of its operating environment and times which indicate that humans will likely be adjacent to the AED 100, then the process follows the "No" branch in which the routine terminates and the process returns to step 1021 of FIG. 10. If the inquiry to decision step 1118 is positive, then the "Yes" branch is followed to step 1121 in which the ASI processor 210 determines, or it may access predetermined values associated with class(es) of environments for, an optimal range of the hours and/or days of operation for the alarm activation windows 702 based on the input received from an operator as described in connection with decision step 1118.

Subsequently, in step 1124, the ASI processor 210 can then determine, or it may access predetermined values associated with class(es) of environments for, an optimal frequency and/or pattern of the alarm activation windows 702 that will occur between the end points of the hour ranges and day ranges calculated in step 1121. This means that the ASI processor 210 will not schedule any alarm activation windows 702 outside of the end points of the hour range and days range.

For example, if the AED 100 is deployed in a typical office environment in which the most humans are present or are adjacent to the AED 100 during the hours of nine AM to five PM, Monday through Friday, then the ASI processor 210 may not schedule alarm activation windows 702 to occur on Saturdays or Sundays, or between the hours of five PM to nine AM, Monday through Friday. In this way, additional battery power can be conserved since the chances that any alerts will be detected by human operators will likely occur during peak hours in which humans are working or are present and adjacent to a particular AED 100. After step 1124, the routine ends and the process returns to step 1021 of FIG. 10.

FIG. 12 illustrates a logical flow diagram 500 of a method for reducing power consumption by an active status indicator (ASI) and extending battery life for a host system by monitoring the conditions of the surrounding environment for an AED. Logical flow diagram 500 highlights some key functional features of ASI processor 210.

Step 510 is a waiting step. ASI processor 210 can operate by predominantly waiting in a power saving sleep mode to be woken by events that it acts upon briefly before returning to the sleep mode. In the exemplary embodiment of the method illustrated in FIG. 12, three events may wake ASI processor 210 from its sleep mode. These events include, but are not limited to, a power button event, an indicator timer event based on a predetermined schedule such as described above in connection with FIG. 10, or a self test event. After handling whichever event awakens ASI processor 210 from the sleep mode of step 510, the ASI processor 210 can transition back through step 580 into the sleep mode of step 510 where ASI processor 210 waits for the next wake event.

In decision step 520, ASI processor 210 determines what type of event woke it from sleep mode. If the wake event was power button 130 being pressed, the ASI processor 210 performs step 523 enabling host processor 410 into its operational mode. In operational mode, host processor 410 is powered on to perform the main operations of the host system. For example, when the host system is AED 100, the main operations comprise patient heart rhythm analysis and possible delivery of defibrillation shocks to the patient. After enabling the host processor 410 into operational mode, ASI processor 210 may continue its operation according to the method 500 in parallel to operational functions of the host processor 410. However, host processor 410, while in its operational mode, may preempt use of indicators 420 or sensors 430 for operational functions. As examples, while in operational mode, host processor 410 may use speaker 160 to provide instructions to the operator, or microphone 340 to record audio of the rescue attempt.

During step 523, the host processor 410 may also query the ASI processor 210 for the environmental conditions of the AED 100 that are sensed by the ASI processor 210. The host processor 410 can use these environmental conditions sensed by the ASI processor 210 to adjust intensity level, duration of powering, or duration between powering of its operational indicators such as a speaker 160 or a LED 235.

Also during step 523, the host processor 410 may request the ASI processor 210 to run all self tests so that the current condition of all AED elements are presented to the operator. In this way, an operator will know if the AED 100 can be used to administer life-saving shocks to a patient.

If the wake event determined in step 520 is a test event, ASI processor 210 transitions to routine 526 where internal self tests are initiated by ASI processor 210 and performed by ASI processor 210, host processor 410, or other system circuitry. Routine 526 generally corresponds with Method 1000 of FIG. 10 as discussed above. A test event may be caused by a periodic test timer based on a schedule calculated by the ASI processor 210 in FIG. 10, a user request, or an external event such as the insertion of a new battery. Once self tests are completed, ASI processor 210 transitions from testing step 526 into step 580 where ASI processor 210 returns to sleep mode of step 510.

If the wake event determined in step 520 is an indicator timer, such as a scheduled activation window 702, ASI processor 210 transitions to decision step 529 where it is determined if the ambient environment should be sensed on this timer cycle. In a preferred, yet exemplary embodiment, the ambient environment is sensed less frequently than the indicator is powered. That is, the inventive ASI system may not detect environmental conditions every time a status indicating event is scheduled to occur. The inventive ASI system can detect environmental conditions such as ambient light conditions or ambient acoustic noise conditions at a rate that can be different than the frequency set for an indicating event. That is, the environment may be sensed more or less frequently than the indicator is powered. One of ordinary skill in the art will appreciate that such alternate embodiments of the inventive method do not depart from the spirit or scope of the invention.

If it is determined during decision step 529 that the ambient environment is to be sensed, ASI processor 210 transitions to routine 530 where the ambient environment is sensed and then to routine 540 where the intensity, duration, and frequency of indicators are set according to ambient conditions sensed in routine 530. Further details of routines 530 and 540 will be discussed below with respect to FIGS. 13 and 14. If it is determined during decision step 529 instead that the ambient environment is not to be sensed during this timer cycle, the ASI processor 210 transitions directly to step 550.

In decision step 550, ASI processor 210 determines if an indicator event should be performed during the current indicator timer cycle or not. This feature allows the ASI system to slow down the rate of indicator events by skipping indicator cycles. The ASI processor 210 will take into account any scheduled activation windows that may have been calculated in Method 1000 of FIG. 10.

One of ordinary skill in the art will appreciate that this same effect may be achieved by modifying the duration of the indicator timer used to wake the ASI processor 210 from sleep mode 510 into step 530. If no indicator event is to be performed during a specific cycle, ASI processor 210 transitions from decision step 550 into step 580 where ASI processor 210 returns to sleep mode of step 510.

In step 560, ASI processor 210 performs the indicator event. This indication may comprise flashing LED 235, or sounding speaker 160, or some other type of active status indication.

In step 570, ASI processor 210 may analyze indicator reflections to determine if the host system is currently enclosed. Using light sensor 240 to measure the proportion of light emitted by indicator 235 that is reflected directly back into the host system, the ASI processor may determine that there is an enclosure or cover surface immediately outside the host system housing 110. ASI processor 210 may respond to the presence of this surface as an indication that the host system is enclosed and therefore slow or cease visual status indication. Similarly, reflections or echoes of an aural indicator, such as speaker 160, may be detected using microphone 340. These echoes may likewise indicate the presence of an enclosure or cover surface outside the host system.

After step 570, the ASI processor 210 returns to its sleep mode in step 580 in which the host device is in a non-operative state. As noted previously, a non-operative state of the host device usually includes situations in which the host device is performing less than all of its primary functions. For example, a non-operative state for automatic external defibrillators (AEDs) usually includes situations in which an AED is not performing a rescue on a patient. Functions that may occur during non-operative states in AEDs may include self-tests and active status indicator events performed by ASI processor 210.

Referring now to FIG. 13A, a logical flow diagram of routine 530 illustrates the process of sensing ambient environment in an environmentally responsive ASI system with visual indication. In step 610, ASI processor 210 samples photodiode light sensor 240. In step 620, ASI processor 210 stores a measure of the ambient light intensity, or brightness, around the host system using the sampled data from step 610. This stored measure is used later in routine 540. Finally, in step 690, the routine 530 returns to routine 540 of the main process 500 illustrated in FIG. 12.

Referring now to FIG. 13B, a logical flow diagram of routine 530 is illustrated for sensing the ambient environment in an environmentally responsive ASI system with aural indication. In step 650, ASI processor 210 samples microphone 340. In step 660, ASI processor 210 stores a measure of the ambient sound intensity, or loudness, around the host system using the sampled data from step 650. This stored measure is used later in routine 540. Finally, in step 690, the routine 530 returns to routine 540 of the main process 500 illustrated in FIG. 12.

Referring now to FIG. 14A, a logical flow diagram of routine 540A is illustrated for setting indicator intensity in an environmentally responsive ASI system with visual indication 235. In step 710, ASI processor 210 retrieves the stored measure of ambient light intensity from the stored value that was calculated by routine 530. In step 720, ASI processor 210 sets the intensity to be used when flashing the light indicator 235. This setting is made based on the ambient light intensity retrieved in step 710. For example, if the ambient lighting is dim, the ASI processor 210 may set the indicator light 235 intensity to a lower level or if ambient lighting is bright, ASI processor 210 may set indicator light 235 intensity to a higher level.

In addition to these two relative examples of higher and lower light intensities, there may be many levels of intensity available to be set according to many different ambient brightness levels that may be sensed. Indicator brightness levels may be computed from the measured ambient light intensities, or alternatively, value ranges stored in one or more tables present in memory may be used to map measured ambient light intensities to appropriate indicator brightness levels. Finally, in step 790, the routine 540 returns to decision step 550 of the main process 500 illustrated in FIG. 12.

Referring now to FIG. 14B, a logical flow diagram of routine 540B is illustrated for setting indicator intensity in an environmentally responsive ASI system with aural indication via speaker 160. In step 750, ASI processor 210 retrieves the stored measure of ambient sound intensity from the stored value that was calculated by routine 530. In step 760, ASI processor 210 sets the intensity, or volume, to be used when sounding speaker 160 as a status indicator. This setting is made based on the ambient sound intensity retrieved in step 750. For example, if the ambient sound level is high, the ASI processor 210 may set the volume of speaker 160 to a higher level so that it can be heard over the ambient noise.

If the ambient noise level is low, the ASI processor 210 may set the volume of speaker 160 to a lower level. In addition to these two relative examples of higher and lower speaker volume, there may be many levels of volume available to be set according to many different ambient noise levels that may be sensed. Speaker volume levels may be computed from the measured ambient noise intensities, or alternatively, value ranges stored in one or more tables present in memory may be used to map measured ambient noise levels to appropriate speaker volume levels.

Finally, in step 790, the routine 540B returns to decision step 550 of the main process 500 illustrated in FIG. 12. In addition to the functionally of routine 540 setting the volume of speaker 160 for status indication purposes, the host processor 410 may retain these volume settings for speaker 160 during operational mode where it may use speaker 160 to provide instructions or other audio to the operator.

Figure 15:
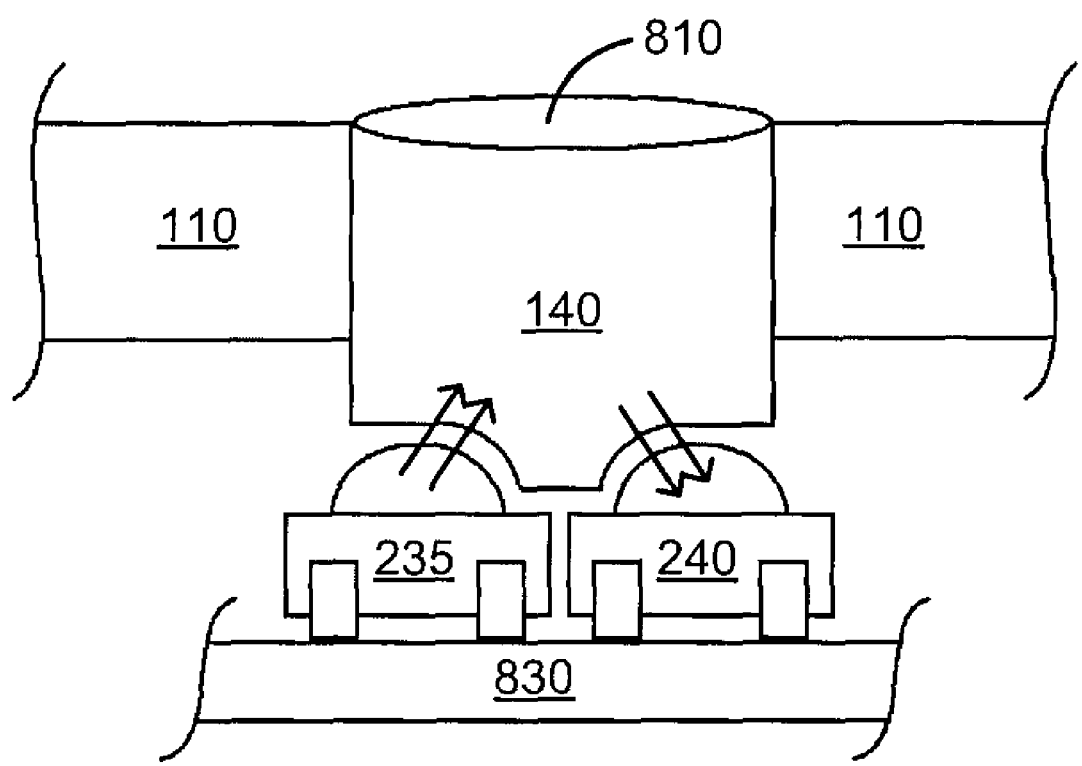
FIG. 15 is a side view illustrating a surface-mounted LED and surface-mounted photodiode both optically coupled to the same light pipe according to one exemplary embodiment of the invention.

Referring now to FIG. 15 which is a side view illustrating surface-mounted LED 235 and surface-mounted photodiode 240 both optically coupled to the same light pipe 140 according to one exemplary embodiment of the invention. Host system housing 110 encloses a light pipe 140 for optically coupling both LED 235 and photodiode 240 to the outside of the system housing 110. However, in other exemplary embodiments (not illustrated), the LED 235 and photodiode 240 may have separate light pipes 140 for propagating light into and out of the host system housing 110.

Light emitted from LED 235 is directed out through the outside surface 810 of the light pipe. Ambient light conditions outside the host system housing 110 may be directed from outside surface 810 of light pipe 140 into photodiode 240.

Both LED 235 and photodiode 240 are surface mounted to printed circuit board 830 where they are in electrical communication with ASI processor 210. Light pipe 140 may simplify system manufacture by enabling the use of surface mount components 235 and 240. An additional benefit of light pipe 140 may detect reflections off of surfaces beyond light pipe surface 810. ASI processor 210 may respond to the presence of these surfaces as an indication that the host system is enclosed and therefore slow or cease visual status indication.

Alternative embodiments of the effective alert generating and environmentally responsive ASI system will become apparent to one of ordinary skill in the art to which the present invention pertains without departing from its spirit and scope. Thus, although this invention has been described in exemplary form with a certain degree of particularity, it should be understood that the present disclosure has been made only by way of example and that numerous changes in the details of construction and the combination and arrangement of parts or steps may be resorted to without departing from the spirit or scope of the invention. Accordingly, the scope of the present invention is defined by the appended claims rather than the foregoing description.

What is claimed is:

1. A method for generating an effective status indicator for an automatic external defibrillator (AED), comprising:
   determining if an element of the AED needs servicing;
   if the element needs servicing, determining a duration of an alert to indicate status of the element for an alarm activation window, wherein each alarm activation window includes multiple alerts and delays between the alerts;
   if the element needs servicing, determining a duration of the delays between the multiple alerts for the alarm activation window; and
   if the element needs servicing, calculating a schedule for multiple alarm activation windows over a specified time period.

2. The method of claim 1, wherein each alarm activation window comprises a magnitude of time less than one hour and occurs only once during any given hour.

3. The method of claim 1, wherein the element comprises at least one of a battery, pads for administering shock to a patient, a display, hardware for executing programs, and software.

4. The method of claim 1, wherein each alert comprises at least one of an audible sound and an illuminated light.

5. The method of claim 4, wherein the audible sound comprises one of a tone and synthesized speech.

6. The method of claim 1, wherein the alerts comprise at least two audible sounds produced by a speaker, a first audible sound indicating status of a first element and a second audible sound indicating status of a second element.

7. The method of claim 1, further comprising determining an optimal range of hours in which to schedule multiple alarm activation windows such that alarm activation windows are not scheduled outside of the optimal range of hours.

8. The method of claim 1, further comprising determining an optimal range of days in which to schedule multiple alarm activation windows such that alarm activation windows are not scheduled outside of the optimal range of days.

9. The method of claim 1, wherein the alerts comprise at least two indicators, a first indicator indicating status of a first element, and a second indicator indicating status of a second element.

10. A method for producing an effective alert to indicate status of an element of an automatic external defibrillator (AED), comprising:

determining if an element of an AED needs servicing;
if the element needs servicing, determining a duration of an alarm to indicate status of the element for an alarm activation window, wherein each alarm activation window includes multiple iterations of the alarm and delays between the iterations of the alarm;
if the element needs servicing, activating the alarm for a series of iterations during the alarm activation window, each alarm activation window comprising an amount of time defined between a start of a first iteration and an ending of a subsequent iteration of the alarm, the alarm comprising an audible sound;
if the element needs servicing, determining a duration of the delays between the multiple iterations of the alarm for the alarm activation window; and
if the element needs servicing, calculating a schedule for multiple alarm activation windows over a specified time period.

11. The method of claim 10, wherein the alarm activation window comprises a magnitude of time less than a half hour.

12. The method of claim 10, wherein the alarm activation window comprises a magnitude of time less than a quarter hour.

13. The method of claim 10, wherein the alarm activation window comprises a magnitude of time less than one minute.

14. The method of claim 10, wherein the element comprises at least one of a battery, pads for administering shock to a patient, a display, hardware for executing programs, and software.

15. The method of claim 10, wherein the alarm further comprises an illuminated light.

16. The method of claim 10 wherein the audible sound comprises one of a tone and synthesized speech.

17. The method of claim 10 wherein the audible sound comprises at least two different sounds, a first sound indicating status for the battery, and a second sound indicating status of another element of the AED other than the battery.

18. The method of claim 10, wherein determining if an element of the AED needs servicing comprises determining if a battery has fallen below a predetermined voltage or current.

19. The method of claim 10, further comprising determining an optimal range of hours in which to schedule multiple alarm activation windows such that alarm activation windows are not scheduled outside of the optimal range of hours.

20. The method of claim 19 wherein determining an optimal range of hours further comprises receiving input regarding hours in which humans are likely to be in the vicinity of the AED.

21. The method of claim 10, wherein the alarm comprises at least two indicators, a first indicator indicating status of a first element, and a second indicator indicating status of a second element.

22. A method for producing an effective alert to indicate status of an element of an automatic external defibrillator (AED) comprising:
determining if an element of an AED needs servicing;
if the element needs servicing, determining a duration of an alarm to indicate status of the element for an alarm activation window, wherein each alarm activation window includes multiple iterations of the alarm and delays between the iterations of the alarm;
if the element needs servicing, activating the alarm for several iterations during the alarm activation window, each alarm activation window comprising an amount of time defined between a start of a first iteration and an ending of a subsequent iteration of the alarm;
if the element needs servicing, determining a duration of the delays between the multiple alerts for the alarm activation window; and
if the element needs servicing, calculating a schedule for multiple alarm activation windows over a specified time period.

23. The method of claim 22, wherein each alarm activation window comprises about thirty seconds in which the alarm is activated about every five seconds for six iterations.

24. The method of claim 22, wherein each alarm activation window occurs at least twice during a time period of sixty minutes.

25. The method of claim 22, wherein the alarm comprises an audible sound produced by a speaker of the AED.

26. The method of claim 22, wherein the alarm comprises a visual indicator.

27. The method of claim 22 wherein the element comprises at least one of a battery, pads for administering shock to a patient, a display, hardware for executing programs, and software.

28. The method of claim 22, further comprising determining a range of hours in which to schedule multiple alarm activation windows such that alarm activation windows are not scheduled outside of the range of hours.

29. The method of claim 28, wherein determining a range of hours comprises receiving input regarding hours in which humans are likely to be in the vicinity of the AED such that alarm activation windows are not scheduled outside of the hours in which humans are likely to be in the vicinity of the AED.

30. The method of claim 22, wherein the alarm comprises at least two indicators, a first indicator indicating status of a first element, and a second indicator indicating status of a second element.

* * * * *